US012152068B2

(12) United States Patent
Kauvar et al.

(10) Patent No.: US 12,152,068 B2
(45) Date of Patent: *Nov. 26, 2024

(54) BINDING MOIETIES FOR BIOFILM REMEDIATION

(71) Applicant: TRELLIS BIOSCIENCE, LLC, Redwood City, CA (US)

(72) Inventors: Lawrence M. Kauvar, San Francisco, CA (US); Stefan Ryser, Menlo Park, CA (US); Angeles Estelles, Belmont, CA (US); Reyna J. Simon, Los Gatos, CA (US); Lauren Opremcak Bakaletz, Columbus, OH (US); Steven David Goodman, Columbus, OH (US)

(73) Assignee: Trellis Bioscience, LLC, Redwood City, CA (US)

( * ) Notice: Subject to any disclaimer, the term of this patent is extended or adjusted under 35 U.S.C. 154(b) by 389 days.

This patent is subject to a terminal disclaimer.

(21) Appl. No.: 17/569,377

(22) Filed: Jan. 5, 2022

(65) Prior Publication Data

US 2022/0259294 A1 Aug. 18, 2022

Related U.S. Application Data

(60) Continuation of application No. 16/746,708, filed on Jan. 17, 2020, now Pat. No. 11,248,040, which is a division of application No. 16/181,260, filed on Nov. 5, 2018, now Pat. No. 10,570,193, which is a division of application No. 15/144,681, filed on May 2, 2016, now Pat. No. 10,233,234, which is a continuation-in-part of application No. 15/042,061, filed on Feb. 11, 2016, now abandoned, and a continuation-in-part of application No. 14/789,842, filed on Jul. 1, 2015, now abandoned, which is a continuation-in-part of application No. 14/668,767, filed on Mar. 25, 2015, now abandoned, which is a continuation-in-part of application No. 14/497,147, filed on Sep. 25, 2014, now abandoned.

(60) Provisional application No. 61/926,828, filed on Jan. 13, 2014, provisional application No. 61/883,078, filed on Sep. 26, 2013.

(51) Int. Cl.
| | |
|---|---|
| *C07K 16/12* | (2006.01) |
| *A61K 35/12* | (2015.01) |
| *A61K 39/00* | (2006.01) |
| *A61K 39/40* | (2006.01) |
| *A61K 45/06* | (2006.01) |
| *A61K 49/00* | (2006.01) |
| *C07K 14/31* | (2006.01) |
| *C12N 15/86* | (2006.01) |
| *C12Q 1/18* | (2006.01) |
| *G01N 33/566* | (2006.01) |
| *G01N 33/569* | (2006.01) |

(52) U.S. Cl.
CPC .......... *C07K 16/1271* (2013.01); *A61K 39/40* (2013.01); *A61K 45/06* (2013.01); *A61K 49/00* (2013.01); *C07K 14/31* (2013.01); *C07K 16/1214* (2013.01); *C07K 16/1228* (2013.01); *C07K 16/1242* (2013.01); *C07K 16/1275* (2013.01); *C12Q 1/18* (2013.01); *G01N 33/566* (2013.01); *G01N 33/56911* (2013.01); *A61K 35/12* (2013.01); *A61K 39/00* (2013.01); *A61K 2039/505* (2013.01); *C07K 2317/21* (2013.01); *C07K 2317/33* (2013.01); *C07K 2317/34* (2013.01); *C07K 2317/76* (2013.01); *C07K 2317/92* (2013.01); *C07K 2319/00* (2013.01); *C12N 15/86* (2013.01); *G01N 2333/195* (2013.01); *G01N 2333/21* (2013.01); *G01N 2333/245* (2013.01); *G01N 2333/26* (2013.01); *G01N 2333/285* (2013.01); *G01N 2469/10* (2013.01)

(58) Field of Classification Search
None
See application file for complete search history.

(56) References Cited

U.S. PATENT DOCUMENTS

| | | |
|---|---|---|
| 6,846,651 B2 | 1/2005 | Fleischmann |
| 7,413,868 B2 | 8/2008 | Kauvar |
| 7,939,344 B2 | 5/2011 | Kauvar |

(Continued)

FOREIGN PATENT DOCUMENTS

| | | |
|---|---|---|
| JP | 2005519998 | 7/2005 |
| JP | 2006506441 | 2/2006 |

(Continued)

OTHER PUBLICATIONS

Adams, et al., "Epitope-mapping the immune response of children with otitis media and adults with chronic obstructive pulmonary disease to the PilA protein of nontypeable Haemophilus influenzae type IV pilus", Immunology, 9th International Symposium on Recent Advances in Otitis Media; St. Pete Beach, FL, 2007, p. 356 (1 page).

(Continued)

*Primary Examiner* — Brian Gangle
*Assistant Examiner* — Lakia J Jackson-Tongue
(74) *Attorney, Agent, or Firm* — FisherBroyles, LLP; Jason M. Pass

(57) ABSTRACT

Binding agents able to disrupt bacterial biofilms of diverse origin are described, including monoclonal antibodies secreted by human B lymphocytes. Methods to prevent formation of or to dissolve biofilms with these binding agents are also described. Immunogens for eliciting antibodies to disrupt biofilms are also described.

18 Claims, 4 Drawing Sheets

Specification includes a Sequence Listing.

(56) References Cited

U.S. PATENT DOCUMENTS

| | | | |
|---|---|---|---|
| 8,933,029 | B2 | 1/2015 | Mcnicol |
| 8,999,291 | B2 | 4/2015 | Goodman |
| 9,017,656 | B2 | 4/2015 | Hancock |
| 9,155,792 | B2 | 10/2015 | Cottarel |
| 10,233,234 | B2 * | 3/2019 | Kauvar ............... A61K 39/40 |
| 2002/0132753 | A1 | 9/2002 | Rosen |
| 2003/0060410 | A1 | 3/2003 | Tracey |
| 2003/0099602 | A1 | 5/2003 | Levin |
| 2003/0229065 | A1 | 12/2003 | Levy |
| 2004/0202670 | A1 | 10/2004 | Apicella |
| 2005/0049402 | A1 | 3/2005 | Babcook |
| 2005/0131222 | A1 | 6/2005 | Fleischmann |
| 2005/0221439 | A1 | 10/2005 | Bakaletz |
| 2006/0030539 | A1 | 2/2006 | Nick |
| 2006/0099207 | A1 | 5/2006 | Wu |
| 2006/0121047 | A1 | 6/2006 | Tracey |
| 2006/0228384 | A1 | 10/2006 | Eldridge |
| 2006/0240045 | A1 | 10/2006 | Berthet |
| 2007/0154529 | A1 | 7/2007 | Bullerdiek |
| 2007/0264256 | A1 | 11/2007 | Bakaletz |
| 2009/0029929 | A1 | 1/2009 | Nakajima |
| 2010/0291177 | A1 | 11/2010 | Hermans |
| 2011/0236306 | A1 | 9/2011 | Goodman |
| 2011/0293624 | A1 | 12/2011 | Bakaletz |
| 2012/0128701 | A1 | 5/2012 | Goodman |
| 2015/0086542 | A1 | 3/2015 | Goodman |
| 2015/0086561 | A1 | 3/2015 | Kauvar |
| 2015/0166641 | A1 | 6/2015 | Goodman |
| 2015/0197558 | A1 | 7/2015 | Kauvar |
| 2015/0299298 | A1 | 10/2015 | Kauvar |
| 2016/0194384 | A1 | 7/2016 | Goodman |

FOREIGN PATENT DOCUMENTS

| | | |
|---|---|---|
| JP | 2006506467 | 2/2006 |
| JP | 2008520552 | 6/2008 |
| JP | 2013529893 | 7/2013 |
| WO | 0047104 | 8/2000 |
| WO | 03026691 | 4/2003 |
| WO | 2004014418 | 2/2004 |
| WO | 2004044001 | 5/2004 |
| WO | 2004072094 | 8/2004 |
| WO | 2005025604 | 3/2005 |
| WO | 2006017816 | 2/2006 |
| WO | 2006083301 | 8/2006 |
| WO | 2006114805 | 11/2006 |
| WO | 2007001422 | 1/2007 |
| WO | 2009006699 | 1/2009 |
| WO | 2011123396 | 10/2011 |
| WO | 2012034090 | 3/2012 |
| WO | 2014201305 | 2/2014 |
| WO | 2015038339 | 3/2015 |
| WO | 2015048484 | 4/2015 |

OTHER PUBLICATIONS

Adams, L., et al., "Epitope-mapping the immune response of children with otitis media and adults with chronic obstructive pulmonary disease to the PilA protein of nontypeable Haemophilus influenzae type IV pilus," 107th General Meeting, American Society for Microbiology; Toronto, ON, 2007.

Advisory Action for U.S. Appl. No. 15/078,987, dated Mar. 10, 2017, 3 pages.

Advisory Action for U.S. Appl. No. 15/078,987, dated Mar. 29, 2017, 3 pages.

Andersson, U., et al., "HMGB1 Is a Therapeutic Target for Sterile Inflammation and Infection," Annu. Rev. Immunol. 29:139-162 2011.

Bakaletz, L.O., "New strategies to target bacterial biofilms," 28th Annual North American Cystic Fibrosis Conference (NACFC), Atlanta, GA, Oct. 9-11, 2014 (presentation}.

Bakaletz, L., "Biofilms can be dispersed by focusing the immune system on a common family of bacterial nucleoid associated proteins," 6th ASM Conference on Biofilms, Miami, FL, Sep. 29-Oct. 4, 2012 (presentation).

Bakaletz, L., et al., "Protection against Development of Otitis Media Induced by Nontypeable Haemophilus influenzae by Both Active and Passive Immunization in a Chinchilla Model of Virus-Bacterium Superinfection," Infecion and Immunity 67(6): 2746-2762, 1999.

Bakaletz, L., et al., "Relative immunogenicity and efficacy of two synthetic chimeric peptides of fimbrin as vaccinogens against nasopharyngeal colonization by nontypeable Haemophilus influenzae in the chincilla," Vaccine 15(9):955-961, 1997.

Barve, M., et al., "Cloning and characterization of the mating type (MAT) locus from Ascochyta rabiei (teleomorph: Didymella rabiei) and a MAT phylogeny of legume-associated *Ascochyta* spp.," Fungal Genetics and Biology 39(2):151-167, 2003.

Bass, J., et al., "Extracellular DNA: A Major Proinflammatory Component of Pseudomonas aeruainosa Biofilms," The Journal of Immunology 184:6386-6395, 2010.

Beech, I., et al., "Microbe-surface interactions in biofouling and biocorrosion processes", International MicrobioloQY (2005) 8: 157-168.

Brandstetter, et al., "Antibodies directed against integration host factor mediate biofilm clearance from Nasopore", Laryngoscope., May 13, 2013, 123(11): 2626-2632.

Brockson, et al., "Evaluation of the kinetics and mechanism of action of anti-integration host factor-mediated disruption of bacterial biofilms", Mol Microbiol., Aug. 19, 2014, vol. 93, pp. 1246-1258, XP055147799.

Catlin, B.W., "Extracellular Deoxyribonucleic Acid of Bacteria and a Deoxyribonuclease Inhibitor," Science, vol. 124, pp. 441-442 (Jun. 1956).

Chen, C., et al., "Substrate specificity of Helicobacter pylori histone-like HU protein is determined by insufficient stabilization of DNA flexure points", Biochem J. (2004) 383, pp. 343-351.

Chen, et al., Int. J. Mol. Sci. 2013; 14: 18488-18501.

Cho, J., et al., "The modulation of the biological activities of mitochondrial histone Abf2p by yeast PKA and its possible role in the regulation of mitochondrial DNA content during glucose repression," Biochimica et Biophysica Acta 1522(3):175-186, 2001.

Cohavy, O., et al., "Identification of a Novel Mycobacterial Histone H1 Homologue (HupB) as an Antigenic Target of pANCA Monoclonal Antibody and Serum Immunoglobulin A from Patients with Cohn's Disease," Infection and Immunity 67(12):6510-6517, 1999.

Collarini, E., et al., "Potent High-Affinity Antibodies for Treatment and Prophylaxis of Respiratory Syncytial Virus Derived from B Cells of Infected Patients", The Journal of Immunology, 2009, 183: 6338-6345.

Dalai, B., et al., "Histone-like protein H-NS regulates biofilm formation and virulence of Actinobacillus pleuropheumoniae", Microbial Pathogenesis 46(2009) 128-134.

Donlan, et al., "Biofilms: survival mechanisms of clinically relevant microorganisms," Clin. Microbiol. Rev. (2002) 15(2):167-193.

Eboigbodin, K., et al., "Characterization of the Extracellular Polymeric Substances Produced by *Escherichia coli* Using Infrared Spectroscopic Proteomic, and Aggregation Studies", Biomacromolecules 2008, 9, 686-695.

Estelles, et al., "A High-Affinity Native Human Antibody Disrupts Biofilm from *Staphlococcus aureus* Bacteria and Potentiates Antibiotic Efficacy in a Mouse Implant Infection Model," Antimicrob. Agents Chemother. (2016) 60(4):2292-2301.

Estrela, A., et al., "Combining Biofilm-Controlling Compounds and Antibiotics as a Promising New Way to Control Biofilm Infections," Pharmaceuticals 3:1374-1393, 2010.

Falciola, L., et al., "Mutational analysis of the DNA binding domain A of chromosomal protein HMG1 ," Nucleic Acids Research 22(3):285-292, 1994.

Fan, Z., et al., "HMG2 Interacts with the Nucleosome Assembly Protein SET and Is a Target of the Cytotoxic T-Lymphocyte Protease Granzyme A," Molecular and Cellular Biology 22(8) :2810-2820, 2002.

Final Office Action in U.S. Appl. No. 13/073,782, dated Mar. 27, 2014.

(56) References Cited

OTHER PUBLICATIONS

Final Office Action in U.S. Appl. No. 13/229,575, dated Aug. 29, 2013.
Final Office Action in U.S. Appl. No. 13/229,575, dated Sep. 19, 2014.
Final Office Action in U.S. Appl. No. 14/493,051, dated Oct. 7, 2016.
Final Office Action in U.S. Appl. No. 14/535,254, dated Jun. 9, 2017.
Final Office Action in U.S. Appl. No. 14/535,254, dated Mar. 25, 2016.
Final Office Action in U.S. Appl. No. 14/885,800, dated May 29, 2018.
Final Office Action in U.S. Appl. No. 14/885,800, dated May 4, 2017.
Final Office Action in U.S. Appl. No. 14/967,228, dated Nov. 22, 2017.
Final Rejection for U.S. Appl. No. 15/078,987, dated Dec. 28, 2016, 12 pages.
Garcia-Contreras, et al., "Protein Translation and Cell Death: The Role of Rare tRNAs in Biofilm Formation and in Activating Dormant Phage Killer Genes," PLoS One (2008) 3(6):e2394, 15 pages.
George, A., et al., "Cystic fibrosis infections: treatment strategies and prospects," FEMS Microbial Lett. 300:153-164, 2009.
Gerstel, U., et al., "Complex Regulation of csgD Promoter Activity by Global Regulatory Proteins," Molecular Microbiology 49(3):639-654, 2003.
Goldenberg, et al., "Genetic and biochemical analysis of IHF/HU hybrid proteins", BioChimie, vol. 76, No. 10-11, Jan. 1, 1994, pp. 941-950.
Goodman, S., et al., "Biofilms can be dispersed by focusing the immune system on a common family of bacterial nucleoid-associated proteins", Mucosal Immunology, Nature Publishing Group, US, (Nov. 1, 2011), vol. 4, No. 6, doi:10.1038/MI.2011.27, ISSN 1933-0219, pp. 625-637.
Goodman, S., et al., "In Vitro Selection of Integration Host Factor Binding Sites", Journal of Bacteriology, May 1999, pp. 3246-3255.
Goodman, S., et al., "Replacement of Integration Host Factor Protein-induced DNA Bending by Flexible Regions of DNA," The Journal of Biological Chemistry 274(52):37004-37011, 1999.
Goodman, S.D., "A new immunotherapeutic approach that disperses biofilms", Banff Conference on Infectious Diseases, Banff, Alberta, Canada, May 18, 2012 (presentation).
Goodman, S.D., "Making and breaking biofilms," Ohio Branch American Society for Microbiology Annual Meeting, Columbus, OH, Apr. 11-12, 2014 (presentation).
Goodman, S.D., "Nucleoprotein complexes in the extracellular matrix are critical for the structural integrity of bacterial biofilms," 112th General Meeting, American Society for Microbiology, San Francisco, CA, Jun. 18, 2012 (presentation).
Goodman, S.D., "The DNABII family of proteins: Diagnostic markers and therapeutic targets of bacterial biofilms," International Congress on Bacteriology and Infectious Disease, Baltimore, MD, Nov. 21, 2013.
Goshima, et al., "Chimeric HU-IHF proteins that alter DNA-binding ability," Gene, vol. 118, No. 1, Sep. 1, 1992, pp. 97-102.
Govan, J., et al., "Microbial pathogenesis in cystic fibrosis: mucoid Pseudomonas aeruginosa and Burkholderia cepacia," Microbiol. Rev. 60(3):539-574, 1996.
Granston, A., et al., "Characterization of a Set of Integration Host Factor Mutants Deficient for DNA Binding," J. Mol. Biol. 234:45-59, 1993.
Greenspan, N., et al., "Defining epitopes: It's not as easy as it seems," Nature Biotechnology 17:936-937, 1999.
Gustave, et al., "Biofilms recovered from the sputum of CF patients contain the bacterial protein integration host factor (IHF)," Abstract 25th Annual North American Cystic Fibrosis Conference, Anaheim, CA, Nov. 3-5, 2011.
Gustave, J., et al., "Targeting bacterial integration host factor to disrupt biofilms associated with cystic fibrosis," Journal of Cystic Fibrosis 12(4):384-389, 2013.
Hall-Stoddley, L., et al., "Evolving concepts in biofilm infections", Cellular Microbiology, 11(7)1034-1043, 2009.
Hall-Stoodley, L., et al., "Characterization of biofilm matrix, degradation by DNase treatment and evidence of capsule down regulation in Streptococcus pneumoniae clinical isolates," BMC Microbiology 8:173, 16 pages, 2008.
Hall-Stoodley, L., et al., "Direct Detection of Bacterial Biofilms on the Middle-Ear Mucosa of Children With Chronic Otitis Media", JAMA Jul. 12, 2006; 296(2): 202-2011.
Haluzi, H., et al., "Genes Coding for Integration Host Factor Are Conserve in Gram-Negative Bacteria," Journal of Bacterioloqy, 173(19), pp. 6297-6299 (Oct. 1991).
Harley, V., et al., "The Molecular Action and Regulation of the Testis-Determining Factors, SRY (Sex-Determining Region on the Y Chromosome) and SOX9 [SRY-Related High-Mobility Group (HMG) Box 91," Endocrine Reviews 24(4):466-487, 2003.
Haruta, I., et al., "A Possible Role of Histone-Like DNA-Binding Protein of Streptococcus intermedius in the Pathogenesis of Bile Duct Damage in Primary Biliary Cirrhosis," Clinical Immunology 127(2):245-251, 2008.
Haruta, I., et al., "Long-term bacterial exposure can trigger nonsuppurative destructive cholangitis associated with multifocal epithelial inflammation," Laboratory investigation 90:577-588, 2010.
Haruta, I., et al., "A possible role of histone-like DNA-binding protein of Streptococcus intermedius in the pathogenesis of bile duct damage in primary biliary cirrhosis", Clinical Immunology, 2008, 127, pp. 245-251.
Hoyle, B., et al., "Bacterial Resistance to Antibiotics: The Role of Biofilms," Prog. Drug Res., 37, pp. 91-105 (1991).
International Search Report and Written Opinion for PCT/US14/57771, mailed Mar. 20, 2015, 12 pages.
International Search Report and Written Opinion for PCT/US2014/042201, dated Nov. 28, 2014.
International Search Report and Written Opinion for PCT/US2016/024107, dated Jul. 27, 2016, 8 pages.
Janeway, C., et al., "Manipulating the immune response to fight infection," Immunobiology: The Immune System in Health and Disease, 5th ed. (2001 ); retrieved online from https://www.ncbi.nlm.nih.gov/books/NBK27131/.
Jiao, Y., et al., "Identification of Biofilm Matrix-Associated Proteins form an Acid Mine Drainage Microbial Community", Applied and Environmental Microbiology, Aug. 2011, vol. 77, No. 15, pp. 5230-5237.
Jodar, L., et al., "Development of vaccines against meningococcal disease," Lancet 359:1499-150, 2002.
Johnson, R., et al., "Chapter 8: Bending and Compaction of DNA by Proteins," Protein-Nucleic Acid Interactions: Structural Biology, pp. 176-220 (2008).
Jurcisek, J., et al., "Biofilms Formed by Nontypeable Haemophilus influenza In Vivo Contain both Double-Stranded DNA and Type IV Pilin Protein", Journal of Bacteriology, vol. 189, No. 10, May 2007, pp. 3868-3875.
Jurcisek, J., et al., "Role of Sialic Acid and Complex Carbohydrate Biosynthesis in Biofilm Formation by Nontypeable Haemophilus influenza in the Chinchilla Middle Ear", Infection and Immunity, vol. 73, No. 6, Jun. 2005, pp. 3210-3218.
Justice, S., et al., "Aberrant Community Architecture and Attenuated Persistence of Uropathogenic Escherichia coli in the Absence of Individual IHF Subunits," PLoS One 7(10):e48349, 1-15, 2012.
Kamashev, D., et al., "The histone-like protein HU binds specifically to DNA recombination and repair intermediates," The EMBO Journal 19(23):6527-6535, 2000.
Kennedy, B., et al., "Passive Transfer of Antiserum Specific for Immunogens Derived from a Nontypeable Haemophilus influenzae Adhesin and Lipoprotein D Prevents Otitis Media after Heteroloqous Challenge," Infection and Immunity 68(5):2756-2765, 2000.
Kim, D., et al., "Beta-Arm flexibility of HU from Staphylococcus aureus dictates the DNA-binding and recognition mechanism," Acta Cryst. D70:3273-3289, 2014.

(56) References Cited

OTHER PUBLICATIONS

Kim, N., et al., "Proteins Released by Helicobacter pylori in Vitro," Journal of Bacteriology, Nov. 2002, vol. 184, No. 22, pp. 6155-6162.

Kirketerp-Moller, K., et al., "Distribution, Organization, and Ecology of Bacteria in Chronic Wounds," Journal of Clinical Microbiology 46(8):2717-2722, 2008.

Kornbilt, B., et al., "The genetic variation of the human HMG1 gene," Tissue Antigens 70:151-156, 2007.

Kyd, J., et al., "Efficacy of the 26-Kilodalton Outer Membrane Protein and Two P5 Fimbrin-Derived Immunogens To Induce Clearance of Nontypeable Haemophilus influenzae from the Rat Middle Ear and Lungs as Well as from the Chinchilla Middle Ear and Nasopharynx," Infection and Immunity 71(8):4691-4699, 2003.

Labbe, E., et al., "Association of Smads with lymphoid enhancer binding factor 1/T cell-specific factor mediates cooperative signaling by the transforming growth factor-13 and Wnt pathways," Proc. Natl. Acad. Sci. USA 97(15):8358-8363, 2000.

Lappann, et al., "A dual role of extracellular DNA during biofilm formation of Neisseria meningitidis." Molecular microbiology. 2010;75(6):1355-71.

Lebeaux, D., et al., "From in vitro to in vivo Models of Bacterial Biofilm-Related Infections," Pathogens 2013, 2, 288-356.

Li, L., et al., "Retroviral cDNA Integration: Stimulation by HMG I Family Proteins," Journal of Virology 74(23):10965-10974, 2000.

Liu, D., et al., "Histone-like DNA binding protein of *Streptococcus intermedius* induces the expression of pro-inflammatory cytokines in human monocytes via activation of ERK1 /2 and JNK pathways," Cellular Microbiology 10(1 ):262-276, 2008.

Liu, D., et al., "The essentiality and involvement of *Streptococcus intermedius* histone-like DNA-binding protein in bacterial viability and normal growth," Molecular Microbiology 68(5) :1268-1282, 2008.

Lunsford, R., et al., "DNA-Binding Activities in *Streptococcus gordonii*: Indentification of a Receptor-Nickase and a Histonelike Protein," Current Microbiology vol. 32 (1996), pp. 95-100.

Malhotra, et al., "Defining the functional epitopes of Integration Host Factor (IHF) to develop a novel biofilm-focused immunotherapeutic against nontypeable Haemophilus influenzae-induced chronic and recurrent," Otitis media, Abst. 18th International Symposium on Recent Advances in Otitis Media, National Harbor, MD, Jun. 7-11, 2015.

Malhotra, et al., "Fine mapping the functional epitopes within integration host factor, a novel immunotherapeutic target for NTH I-induced diseases of the airway," 18th International Symposium on Recent Advances in Otitis Media, National Harbor, MD, Jun. 7-11, 2015 (poster).

Malhotra, et al., "Fine mapping the functional epitopes within integration host factor, a novel therapeutic target for nontypeable Haemophilus influenza-induced diseases of the respiratory tract," Abst. 12th Annual AMA Research Symposium, Dallas, TX, Nov. 7, 2014.

Malhotra, et al., "Identification of immunoprotective domains within the bacterial DNA-binding protein, integration host factor," Abst. 20th Annual Midwest Microbial Pathogenesis Meeting. The Ohio State University, Columbus, OH, Aug. 23-25, 2013.

Malhotra, et al., "Identification of immunoprotective domains within the bacterial DNA-binding protein, integration host factor," Seventh Extraordinary International Symposium on Recent Advances in Otitis Media, Stockholm, Sweden, Jun. 15, 2013 (presentation).

Martinez-Antonio, A., et al., "Functional organization of *Escherichia coli* transcriptional requlatory network", J. Mol. Biol. 381 :238-247, 2008.

Meluleni, G., et al., "Mucoid Pseudomonas aeruginosa Growing in a Biofilm In Vitro Are Killed by Opsonic Antibodies to the Mucoid Exopolysaccharide Capsule but Not by Antibodies Produced During Chronic Lung Infection in Cystic Fibrosis Patients," J. Immunology 155:2029-2038, 1995.

Mouw, K., et al., "Shaping the Borrelia burgdorferi genome: crystal structure and binding properties of the DNA-bending protein Hbb," Molecular Microbiology 63(5):1319-1330, 2007.

Mukherjee, J., et al., "Quantitative protein expression and cell surface characteristics of *Escherichia coli* MG1655 biofilms," Proteomics 2011, vol. 11,39-351.

Murphy, T., et al., "Biofilm formation by nontypeable Haemophilus influenzae: strain variablitiy, outer membrane antigen expression and role of pili," BMC Microbiology 2002,2:7, 8 pgs.

Murphy, T., et al., "Microbial Interactions in the Respiratory Tract," The Pediatric Infectious Disease Journal 28:S121-S126, 2009.

Nakamura, Y., et al., "HMG Box A in HMG3 Protein Functions as a Mediator of DNA Structural Alteration Together with Box B," J. Biochem. 1129:643-651, 2001.

Nash, H., et al., "Overproduction of *Escherichia coli* integration Host Factor, a Protein with Nonidentical Subunits," Journal of Bacteriology 169(9):4124-4127, 1987.

NCBI Genebank: P0A6Y1 (Sep. 13, 2005).

Non-Final Office Action for U.S. Appl. No. 14/493,051 dated Mar. 12, 2015.

Non-Final Office Action for U.S. Appl. No. 14/493,051, dated Oct. 8, 2015.

Non-Final Office Action for U.S. Appl. No. 14/535,254, dated Sep. 9, 2015.

Non-Final Office Action in U.S. Appl. No. 13/073,782, dated Jun. 10, 2013.

Non-Final Office Action in U.S. Appl. No. 13/073,782, dated Jun. 25, 2014.

Non-Final Office Action in U.S. Appl. No. 13/229,575, dated Jan. 10, 2013.

Non-Final Office Action in U.S. Appl. No. 13/229,575, dated Mar. 31, 2014.

Non-Final Office Action in U.S. Appl. No. 14/493,051, dated Apr. 28, 2016.

Non-Final Office Action in U.S. Appl. No. 14/493,051, dated Jan. 10, 2017.

Non-Final Office Action in U.S. Appl. No. 14/535,254, dated Jan. 26, 2018.

Non-Final Office Action in U.S. Appl. No. 14/535,254, dated Jul. 10, 2017.

Non-Final Office Action in U.S. Appl. No. 14/885,800, dated Dec. 15, 2017.

Non-Final Office Action in U.S. Appl. No. 14/885,800, dated Oct. 31, 2016.

Non-Final Office Action in U.S. Appl. No. 14/967,228, dated May 19, 2017.

Non-Final Office Action in U.S. Appl. No. 15/078,987, dated Mar. 16, 2018.

Non-final Rejection for U.S. Appl. No. 15/078,987, dated Jul. 14, 2016, 15 pages.

Non-final Rejection for U.S. Appl. No. 15/078,987, dated Jun. 14, 2017, 25 pages.

Notice of Allowability in U.S. Appl. No. 13/073,782, dated Mar. 4, 2015.

Notice of Allowance in U.S. Appl. No. 13/073,782, dated Aug. 19, 2014.

Notice of Allowance in U.S. Appl. No. 14/493,051, dated Apr. 25, 2017.

Notice of Allowance in U.S. Appl. No. 14/493,051, dated Jan. 27, 2017.

Novotny, et al., "Antibodies against the majority subunit of type IV Pili disperse nontypeable Haemophilus influenzae biofilms in a LuxS-dependent manner and confer therapeutic resolution of experimental otitis media", Mol Microbiol., (Feb. 15, 2015), vol. 96, pp. 1-32, XP055318148.

Novotny, L., et al., "Detection and characterization of pediatric serum antibody to the OMP PS-homologous adhesin of nontypeable Haemophilus influenzae during acute otitis media," Vaccine 20(29-30):3590-3597, 2002.

Novotny, L., et al., "Epitope mapping immunodominant regions of the PilA protein of nontypeable Haemophilus influenzae (NTHI) to facilitate the design of two novel chimeric vaccine candidates," Vaccine 28(1):279-289, 2010.

(56) References Cited

OTHER PUBLICATIONS

Novotny, L., et al., "Epitope mapping of the Outer Membrane Protein P5-Homologous Fimbrin Adhesin of Nontypeable Haemophilus influenzas," Infection and Immunity 68(4):2119-2128, 2000.
Novotny, L., et al., "Monoclonal antibodies against DNA-binding tips of DNABII proteins disrupt biofilms in vitro and induce bacterial clearance in vivo", Ebiomedicine, (Aug. 1, 2016), vol. 10, doi:10.1016/j.ebiom.2016.06.022, ISSN 2352-3964, pp. 33-44, XP055352908.
Novotny, L., et al., "Passive immunization with human anti-protein D antibodies induced by polysaccharide protein D conjugates protects chinchillas against otitis media after intranasal challenge with Haemophilus influenzas," Vaccine 24(22):4804-4811, 2006.
Novotny, L., et al., "Structural Stability of Burkholderia cenocepacia Biofilms Is Reliant on eDNA Structure and Presence of a Bacterial Nucleic Acid Binding Protein", PLOS One, (Jan. 1, 2013), vol. 8, No. 6, doi:10.1371/journal.pone.0067629, ISSN 1932-6203, p. 67629, XP055147798.
Novotny, L., et al., "The Fourth Surface-Exposed Region of the Outer Membrane Protein P5-Homologous Adhesin of the Nontypable Haemophilus influenzae Is an Immunodominant But Nonprotective Decoying Epitope," The Journal of Immunology 171 (4):1978-1983.
Oberto, J., et al., "Histones, HMG, HU, IHF: Meme combat," Biochimie 76:901-908, 1994.
Ofran et al., "Automated Identification of Complementarity Determining Regions (CDRs) Reveals Peculiar Characteristics of CDRs and B Cell Epitopes", J Immunol, 181 (9), pp. 6230-6235, Nov. 1, 2008 (Nov. 1, 2008).
Ordway, D., et al., "Evaluation of Standard Chemotherapy in the Guinea Pig Model of Tuberculosis," Antimicrobial Agents and Chemotherapy 54:1820-1833, 2010.
Otto, M., "*Staphylococcus epidermidis*—the 'accidental' pathogen," Nature Reviews Microbiology 7:555-567, 2009.
Pedulla, M., et al., "A novel host factor for integration of mycobacteriophage L5," Proc. Natl. Acad. Sci. USA 93:15411-15416, 1996.
Percival, S., et al., "Biofilms and Wounds: An Oveiview of the Evidence," Advances in Wound Care 4{7}:373-381, 2015.
Petersen, F., et al., "Biofilm Mode of Growth of *Streptococcus intermedius* Favoreed by a Competence-Stimulating Signaling Peptide," Journal of Bateriology, Sep. 2004, Vo1. 186, No. 18, pp. 6327-6331.
Pethe, K., et al., "*Mycobacterium smegmatis* laminin-binding glycoprotein shares epitopes with *Mycobacterium tuberculosis* heparin-binding haemagglutinin," Molecular Microbiology (2001) 39(1 ), 89, 99.
Priyadarshini, et al., "The nucleoid-associated protein HUß affects global gene expression in Porphyromonas gingivalis", Microbiology. 2013; 159(Pt 2):219-29.
Prymula, R., et al., "Pneumococcal capsular polysaccharides conjugated to protein D for prevention of acute otitis media caused by both *Streptococcus pneumonias* and non-typable Haemophilus influenzae: a randomized double-blind efficacy study," Lancet 367(9512):740-748, 2006.
Restriction Requirement in U.S. Appl. No. 13/073,782, dated Feb. 20, 2013.
Restriction Requirement in U.S. Appl. No. 13/229,575, dated Jul. 19, 2012.
Restriction Requirement in U.S. Appl. No. 14/493,051, dated Nov. 7, 2014.
Restriction Requirement in U.S. Appl. No. 14/535,254, dated Mar. 27, 2015.
Rice, P. et al., (Aug. 1996), 1 page; retrieved online from http://www.rcsb.org/pdb/explore.do?structureId=IHF.
Rice, P., et al., "Crystal Structure of an IHF-DNA Complex: A Protein-Induced DNA U-Turn," Cell 87(7):1295-1306, 1996.
Rocco, et al., "Natural antigenic differences in the fucntionally equivalent extracellular DNABI I proteins of bacterial biofilms provide a means for targeted biofilm therapeutics," Molecular Oral Microbioloav (2017) 32:118-130.
Rouviere-Yaniv, et al., "Characterization of a novel, low-molecular-weight DNA-binding protein from *Escherichia coli*", Proceedings of the National Academy of Sciences of the United States of America, 1975;72(9):3428-32. Epublished Sep. 1, 1975. PubMed PMID: 1103148; PMCID: 433007.
Rudikoff, S., et al., "Single amino acid substitution altering antigen-binding specificity," Proc. Natl. Acad. Sci. USA 79(6):1979-1983.
Sapi, E., et al., "Characterization of Biofilm Formation by Borrelia burgdorferi In Vitro," PLOS One 7(10):e44277, 1-11, 2012.
Schwartz, K., et al., "Functional Amyloids Composed of Phenol Soluble Modulins Stabilize *Staphylococcus aureus* Biofilms," PLOS Pathogens 8:e1002744, 1-11, 2012.
Segall, A. et al., "Architectural elements in nucleoprotein complexes: interchangeability of specific and non-specific DNA binding proteins," The EMBO Journal vol. 13 No. 19 pp. 4536-4548, 1994.
Shahrooei, M. et al., "Inhibition of *Staphylococcus epidermidis* Biofilm Formation by Rabbit Polyclonal Antibodies against the SesC Protein," Infection and Immunity, Sep. 2009, vol. 77, No. 9, pp. 3670-3678.
Singh, P., et al., "Quorum-sensing signals indicate that cystic fibrosis lungs are infected with bacterial biofilms," Nature 407(12):762-764, 2000.
Skolnick, J., et al., "From genes to protein structure and function: novel applications of computational aoproaches in the genomic era," Trends in Biotechnology 18:34-39, 2000.
Smith, J., et al., "Cystic Fibrosis Airway Epithelia Fail to Kill Bacteria Because of Abnormal Airway Surface Fluid," Cell 85:229-236, 1996.
Stinson, M., et al., "*Streptococcal histone*-Like Protein: Primary Structure of hlpA and Protein Binding to Lipoteichoic Acid and Epithelial Cells," Infection and Immunity 66(1):259-265, 1998.
Stoltz, D., et al., "Cystic Fibrosis Pigs Develop Lung Disease and Exhibit Defective Bacterial Eradication at Birth," www.ScienceTranslationMedicine.org 2(29):29ra31, 1-8, 2010.
Stros, M., et al., "The HMG-box: a versatile protein domain occurring in a wide variety of DNA-binding proteins," Cell. Mol. Life Sci. 64(19-20):2590-2606, 2007.
Sun, D., et al., "Inhibition of Biofilm Formation by Monoclonal Antibodies against *Staphylococcus epidermindis* RP62A Accumulation-Associated Protein," Clinical & Diagnostic Laboratory Immunology, Jan. 2005, vol. 12, No. 1, pp. 93-100.
Supplementary Partial European Search Report for EP 14847993.4, dated Jun. 7, 2017, 20 pages.
Swinger, K., et al., "IHF and HU: flexible architects of bent DNA," Current Opinion in Structural Biology 2004, 14: 28-35.
Takeda, T., "Polyhistidine Affinity Chromatography for Purification and Biochemical Analysis of Fungal Cell Wall Degrading Enzymes," Affinity Chromatography, Dr. Sameh Maadelin (Ed.), ISBN:978-953-51-0325-7, In Tech, p. 177-186, 2012.
Taudte, S., et al., "Alanine mutagenesis of high-mobility-group-protein-1 box B (HMG1-B)," Biochem. J. 347:807-814, 2000.
Teter, B., et al., "DNA Bending and Twisting Properties of Integration Host Factor Determined by DNA Cyclization," Plasmid 43, 73-84 (2000}.
Tetz, G., et al., "Effect of DNase and Antibiotics on Biofilm Characteristics," Antimicrobial Agents and Chemotherapy 53(3):1204-1209, 2009.
Thomas, J., "HMG1 and 2: architectural DNA-binding proteins," Biochemical Society Transactions 29(Pt 4):395-401, 2001.
U.S. Appl. No. 14/885,800, filed Oct. 2015, Goodman et al.
U.S. Appl. No. 14/967,228, filed Dec. 2015, Goodman et al.
U.S. Office Action on U.S. Appl. No. 14/535,254, dated Aug. 12, 2016.
Van Schaik, E., et al., "DNA Binding: a Novel Function of Pseudomonas aeruginosa Type IV Pili," Journal of Bacteriology, Feb. 2005, vol. 187, No. 4, pp. 1455-1464.
Various prosecution history documents and Information Disclosure Statements for U.S. Appl. No. 15/078,987, dated Oct. 4, 2017, 28 pages.
Whitchurch, et al., "Extracellular DNA Required for Bacterial Biofilm Formation", Science, vol. 295, No. 5559, Feb. 22, 2002, Supplementary Material, 2 pages.

(56) References Cited

OTHER PUBLICATIONS

Winters, B., et al., "Isolation and Characterization of a *Streptococcus pyogenes* Protein that Binds to Basal Laminae of Human Cardiac Muscle," Infection and Immunity, Aug. 1993, vol. 61, No. 8, pp. 3259-3264.

Winther, B., et al., "Location of Bacterial Biofilm in the Mucus Overlying the Adenoid by Light Microscopy," Head & Neck Surgery 135(12): 1239-1245, 2009.

Woischnig, A., et al., "High Affinity Native Human Monoclonal Antibody with Broad Cross-Species Biofilm Disrupting Activity" poster presented at IAAC Meeting on Sep. 20, 2015, available at www.trellisbio.com/assets/docs/ICAAC%20Biofilm%20Poster%2020150920.pdf.

Xiong, et al., Antimicrobial Agent and Chemotherapy, 2017; 61(10): 1-10.

Yoshida, M., Seikagaku Biochemistry 68(12):1829-1834, 1996, Shusaku Yamamoto.

Zulianello, et al., "The HimA and HimD subunits of integration host factor can specifically bind to DNA as homodimers", The EMBO Journal, vol. 13, No. 4, Apr. 1, 1994, pp. 1534-1540.

\* cited by examiner

Figure 2

IHF dimer complexed with DNA

B-cell epitopes of the invention

BINDING MOIETIES FOR BIOFILM REMEDIATION

CROSS-REFERENCE TO RELATED APPLICATIONS

This application is a continuation of U.S. patent application Ser. No. 16/746,708 filed Jan. 17, 2020, which is a divisional of U.S. patent application Ser. No. 16/181,260, filed Nov. 5, 2018, now U.S. Pat. No. 10,570,193, which is a divisional of U.S. patent application Ser. No. 15/144,681, filed May 2, 2016, now U.S. Pat. No. 10,233,234, which is a CIP of Ser. No. 14/789,842, filed Jul. 1, 2015, which is a CIP of Ser. No. 14/668,767, filed Mar. 25, 2015, which is a CIP of Ser. No. 14/497,147, filed Sep. 25, 2014, which claims priority from U.S. Provisional Application No. 61/926,828 filed 13 Jan. 2014 and to U.S. Provisional Application No. 61/883,078, filed Sep. 26, 2013. U.S. application Ser. No. 15/144,681 is also a CIP of U.S. patent application Ser. No. 15/042,061, filed Feb. 11, 2016. The contents of the above applications are incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 12774-131 USS_SeqListing.txt, date recorded: Jan. 5, 2022, size: 37 KB).

TECHNICAL FIELD

The invention relates to methods and compositions for dissolution of biofilms that inhibit immune responses and make bacteria resistant to antibiotics. More specifically, it concerns monoclonal antibodies that are derived from human cells or from transgenic animals expressing human antibody genes or that are humanized forms of antibodies native to other species wherein the affinity for the proteins that are responsible for the structural integrity of such biofilms exceeds the affinity of these proteins for biofilm components. Monoclonal antibodies in general and other binding moieties with this property are also included.

BACKGROUND ART

It is well understood in the art that bacterial infections may lead to formation of biofilms that protect the bacteria from the immune system and lead them to enter a quiescent, slow growth state that makes them resistant to most antibiotics (Donlan, R. M., et al., Clin Microbiol Rev (2002) 15:167-193). The result is persistent, recurrent infections that are very difficult to eliminate. These biofilms include as a major component branched DNA molecules that are held together by specific proteins generally designated DNABII proteins, with homologs found in most bacterial species (Goodman, S. D., et al., Mucosal Immunity (2011) 4:625-637). The substantial homology of these proteins facilitates the cooperative formation of biofilms, a feature that further renders the bacteria problematic from a treatment perspective. The present invention is based on the concept that supplying a binding moiety with sufficiently high affinity for this class of proteins will extract the proteins from the biofilm and thereby provide an effective method of destroying the biofilm by destroying the ability of the protein to bind and hold together the branched DNA. A supplied binding moiety against the DNABII protein may also destroy its ability to bind to other components present in the biofilm.

The binding moieties, of which monoclonal antibodies or fragments thereof are an important embodiment, can be supplied directly to biofilms or used to coat surfaces to provide an immuno-adsorbent for confining the DNABII protein(s). Applications include treatments of bacterial infections by systemic administration, subcutaneous, topical or inhaled administration, as well as reduction of biofouling that affects pipelines and other industrial equipment. Application to corresponding biofilm associated diseases of animals is also part of the present invention.

PCT publication WO2011/123396 provides an extensive discussion of such biofilms and suggests their removal by administering to a subject polypeptides that represent the DNABII protein itself, thus causing the organism to generate antibodies that can destroy the integrity of the biofilm. This document also suggests, in the alternative, supplying the antibodies themselves, either ex vivo to biofilms that exist outside an organism or to a subject to confer passive protection.

This PCT application describes the use of polyclonal antibodies generated against a particular DNABII protein (*E. coli* integration host factor (IHF)) to treat an animal model of the common ear infection (otitis media) and of an animal model for periodontal disease. It also describes generating active immunity by providing the protein, or peptides representing the protein to a subject. There is no disclosure of any monoclonal antibodies with the desired affinity that are directed to this protein. Nor is there any disclosure of binding moieties that show cross-species activity against homologs of the IHF protein. Achieving both properties represents a significant obstacle to discovery of an effective drug. The present invention overcomes these obstacles and provides improved agents for passive immunity.

DISCLOSURE OF THE INVENTION

The invention provides homogeneous compositions of binding moieties, such as aptamers, protein mimics or monoclonal antibodies or fragments thereof, that are particularly effective in binding the DNABII protein and thus effective in dissolving biofilms. Thus, the invention in one aspect is directed to a binding moiety such as a monoclonal antibody (mAb) that has affinity for at least one DNABII protein that exceeds the affinity of branched DNA, a component of biofilms, for said protein. It is particularly preferred that any antibodies to be used systemically be compatible with mammalian subjects, especially human subjects or feline, canine, porcine, bovine, ovine, caprine or equine subjects when proposed for use in these subjects. Such native mAbs have lower risk of binding to other proteins in the body than mAbs from other sources and thus pose lower toxicity risk. Similarly, immunogenicity of mAbs native to a subject is expected to be lower than for other mAb sources thereby facilitating repeated administration. Specific binding moieties illustrated herein contain at least the CDR regions of the heavy chains, and optionally the light chains of the mAb's TRL295, TRL1012, TRL1068, TRL1070, TRL1087, TRL1215, TRL1216, TRL1218, TRL1230, TRL1232, TRL1242 and TRL1245. However, other types of binding moieties, such as aptamers, modifications of antibodies such as camel type single-chain antibodies and the like are also included within the scope of the invention.

The invention is further directed to a method to treat a biofilm associated with an industrial process by using the binding moieties of the invention either to dissolve biofilms or prevent their formation. In this instance, a full variability of binding moieties is suitable, and the species origin of mAb's is not of concern. The binding moieties may also be applied topically on a subject to dissolve biofilms or to prevent their formation. The binding moieties may also be administered systematically for treatment of biofilms.

In still other aspects, the invention is directed to recombinant materials and methods to prepare binding moieties of the invention that are proteins, and to improved recombinant methods to prepare DNABII proteins.

In other aspects, the invention is directed to novel expression systems for DNABII proteins to be used as immunogens and to methods to use these DNABII proteins to identify an agent that reverses drug resistance in multiple species of bacteria. The latter methods comprise evaluating agents for binding activity to the DNABII proteins produced by multiple microbial species.

The invention also relates to specific isolated peptides that span predicted immunogenic epitope regions of the IHFα chain of the *E. coli* DNABII as well as to methods for generating antibodies to IHF proteins by using these peptides as immunogens.

In still another aspect, the invention is directed to a method to treat human or animal diseases for which biofilm causes drug resistance. Examples include: heart valve endocarditis (for which surgical valve replacement is required in the substantial fraction of cases that cannot be cured by high dose antibiotics due to the resistance associated with biofilm), chronic non-healing wounds (including venous ulcers and diabetic foot ulcers), ear and sinus infections, urinary tract infections, pulmonary infections (including subjects with cystic fibrosis or chronic obstructive pulmonary disease), catheter associated infections (including renal dialysis subjects), subjects with implanted prostheses (including hip and knee replacements), and periodontal disease. This method is effective in mammalian subjects in general, and thus is also applicable to household pets. For example, 85% of dogs over the age of 3 have periodontal disease which is difficult to treat due to biofilm (Kortegaard, H. E., et al., *J. Small Anim. Pract.* (2008) 49:610-616). Similarly, the invention has utility for treating farm animals. For example, 98% of cultures from dairy cattle with mastitis display bacterial infections associated with biofilm production: Poliana de Castro Melo, et al., *Brazilian J. Microbiology* (2013) 44:119-124).

BRIEF DESCRIPTION OF THE DRAWINGS

FIG. 2 shows the location of the predicted epitopes of the invention in IHF proteins of various bacterial species.

MODES OF CARRYING OUT THE INVENTION

Figure 1A:
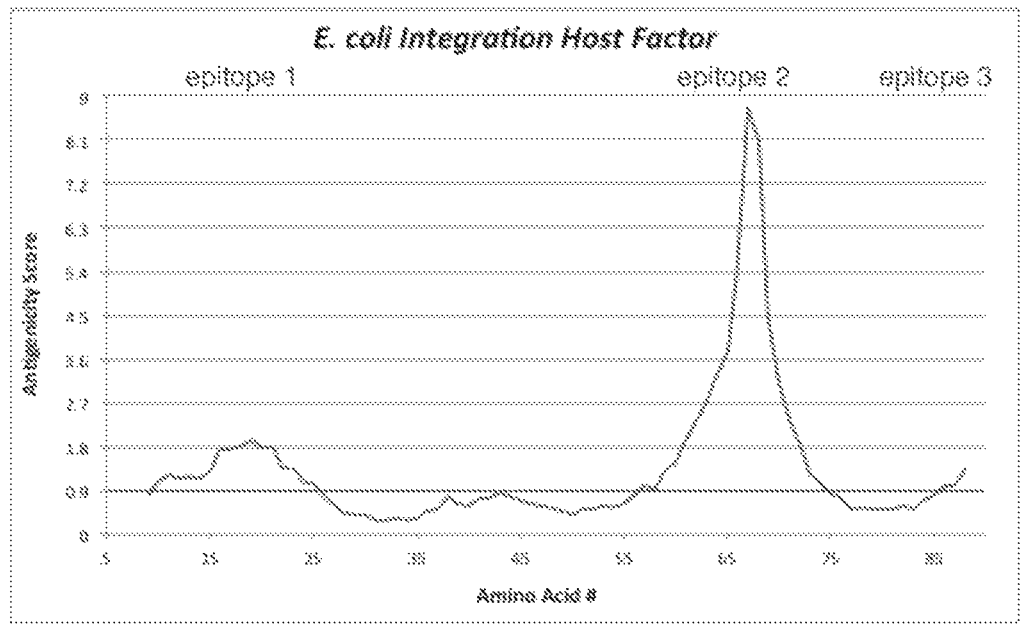
FIG. 1A shows the result of a computational analysis of sites on IHF that are likely to be particularly susceptible to antibody attack (scores above 0.9). Residues 10-25, 56-78, and 86-96 of *Haemophilus influenzae* (Hi) IHF are thereby identified as promising targets.

The invention includes various binding moieties of a monoclonal or homogeneous nature that can dissolve biofilms. "Monoclonal" means that the binding moieties can form a homogeneous population analogous to the distinction between monoclonal and polyclonal antibodies. In one important embodiment, the exemplified binding moieties are mAbs or fragments thereof. In most embodiments, the binding moieties have affinity for at least one DNABII protein in the low nanomolar range—i.e., the Kd is in the range of 10 nM-100 nM including the intervening values, such as 25 nM or 50 nM, but may also be <10 nM as a preferred embodiment.

As the illustrative antibodies disclosed herein in the examples below are derived from humans, the constant regions of these antibodies will be human which offers particular advantages for repeated use in humans. When the subject to be administered the mAb is non-human, it is advantageous for repeated use to administer native mAb's derived from that species. Alternatively, an equivalent of the human variable regions, optionally fused to an Fc region from the host species to be treated, may be used. This variable region may be, in some embodiments, an Fab portion or a single-chain antibody containing CDR regions from both the heavy and light chains. Bispecific forms of these variable regions equivalents can also be constructed, with numerous constructs described in the literature. Although the typical "mAb" will be a protein or polypeptide ("proteins," "polypeptide" and "peptide" are used interchangeably herein without regard to length) for use in subjects, the mAb's may also be supplied via delivery of nucleic acids that then generate the proteins in situ. In addition, nucleic acid molecules that mimic the binding characteristics of these polypeptides or proteins can be constructed—i.e., aptamers can be constructed to bind molecules that are identified as described below by their ability to mimic the binding moieties. Successful mimicry of these aptamers for the protein-based binding moieties can verified both biochemically and functionally to confirm that the affinity of the aptamer is sufficient for therapeutic efficacy.

With respect to protein-based monoclonal binding moieties, in addition to typical monoclonal antibodies or fragments thereof that are immunologically specific for the same antigen, various forms of other scaffolding, including single-chain antibody forms such as those derived from camel, llama or shark could be used as well as antibody mimics based on other scaffolds such as fibronectin, lipocalin, lens crystallin, tetranectin, ankyrin, Protein A (Ig binding domain), or the like. Short structured peptides may also be used if they provide sufficient affinity and specificity, e.g. peptides based on inherently stable structures such as conotoxins or avian pancreatic peptides, or peptidomimetics that achieve stable structures by crosslinking and/or use of non-natural amino acids: Josephson K., et al., *J Am Chem Soc* (2005) 127 (33): 11727-11725). In general, "monoclonal antibody (mAb)" includes all of the foregoing.

As used herein, the term "antibody" includes immunoreactive fragments of traditional antibodies even if, on occasion, "fragments" are mentioned redundantly. The antibodies, thus, include Fab, F(ab')$_2$, F$_v$ fragments, single-chain antibodies which contain a substantially only variable regions, bispecific antibodies and their various fragmented forms that still retain immunospecificity and proteins in general that mimic the activity of "natural" antibodies by comprising amino acid sequences or modified amino acid sequences (i.e., pseudopeptides) that approximate the activity of variable regions of more traditional naturally occurring antibodies.

For the variable regions of mAb's, as is well known, the critical amino acid sequences are the CDR sequences arranged on a framework which framework can vary without necessarily affecting specificity or decreasing affinity to an unacceptable level. Definition of these CDR regions is accomplished by art-known methods. Specifically, the most commonly used method for identifying the relevant CDR regions is that of Kabat as disclosed in Wu, T. T., et al., *J. Exp. Med.* (1970) 132:211-250 and in the book Kabat, E. A., et al. (1983) *Sequence of Proteins of Immunological Interest*, Bethesda National Institute of Health, 323 pages. Another similar and commonly employed method is that of Chothia, published in Chothia, C., et al., *J. Mol. Biol.* (1987) 196: 901-917 and in Chothia, C., et al., *Nature* (1989) 342:877-883. An additional modification has been suggested by Abhinandan, K. R., et al., *Mol. Immunol.* (2008) 45:3832-3839. The present invention includes the CDR regions as defined by any of these systems or other recognized systems known in the art.

The specificities of the binding of the mAb's of the invention are defined, as noted, by the CDR regions mostly those of the heavy chain, but complemented by those of the light chain as well (the light chains being somewhat interchangeable). Therefore, the mAb's of the invention may contain the three CDR regions of a heavy chain and optionally the three CDR's of a light chain that matches it. The invention also includes binding agents that bind to the same epitopes as those that actually contain these CDR regions. Thus, for example, also included are aptamers that have the same binding specificity—i.e., bind to the same epitopes as do the mAb's that actually contain the CDR regions. Because binding affinity is also determined by the manner in which the CDR's are arranged on a framework, the mAb's of the invention may contain complete variable regions of the heavy chain containing the three relevant CDR's as well as, optionally, the complete light chain variable region comprising the three CDR's associated with the light chain complementing the heavy chain in question. This is true with respect to the mAb's that are immunospecific for a single epitope as well as for bispecific antibodies or binding moieties that are able to bind two separate epitopes, for example, divergent DNABII proteins from two bacterial species.

The mAb's of the invention may be produced recombinantly using known techniques. Thus, with regard to the novel antibodies described herein, the invention also relates to nucleic acid molecules comprising nucleotide sequence encoding them, as well as vectors or expression systems that comprise these nucleotide sequences, cells containing expression systems or vectors for expression of these nucleotide sequences and methods to produce the binding moieties by culturing these cells and recovering the binding moieties produced. Any type of cell typically used in recombinant methods can be employed including prokaryotes, yeast, mammalian cells, insect cells and plant cells. Also included are human cells (e.g., muscle cells or lymphocytes) transformed with a recombinant molecule that encodes the novel antibodies.

Bispecific binding moieties may be formed by covalently linking two different binding moieties with different specificities. For example, the CDR regions of the heavy and optionally light chain derived from one monospecific mAb may be coupled through any suitable linking means to peptides comprising the CDR regions of the heavy chain sequence and optionally light chain of a second mAb. If the linkage is through an amino acid sequence, the bispecific binding moieties can be produced recombinantly and the nucleic acid encoding the entire bispecific entity expressed recombinantly. As was the case for the binding moieties with a single specificity, the invention also includes the possibility of binding moieties that bind to one or both of the same epitopes as the bispecific antibody or binding entity/binding moiety that actually contains the CDR regions.

The invention further includes bispecific constructs which comprise the complete heavy and light chain sequences or the complete heavy chain sequence and at least the CDR's of the light chains or the CDR's of the heavy chains and the complete sequence of the light chains.

The invention is also directed to nucleic acids encoding the bispecific moieties and to recombinant methods for their production.

Multiple technologies now exist for making a single antibody-like molecule that incorporates antigen specificity domains from two separate antibodies (bi-specific antibody). Thus, a single antibody with very broad strain reactivity can be constructed using the Fab domains of individual antibodies with broad reactivity to Group 1 and Group 2 respectively. Suitable technologies have been described by Macrogenics (Rockville, MD), Micromet (Bethesda, MD) and Merrimac (Cambridge, MA). (See, e.g., Orcutt, K. D., Ackerman, M. E., Cieslewicz, M., Quiroz, E., Slusarczyk, A. L., Frangioni, J. V., Wittrup, K. D., "A Modular IgG-scFv Bispecific Antibody Topology," *Protein Eng Des Sel.* (2010) 23:221-228; Fitzgerald, J., Lugovskoy, A., "Rational Engineering of Antibody Therapeutics Targeting Multiple Oncogene Pathways," *MAbs.* (2011) 1:3(3); Baeuerle, P. A., Reinhardt, C., "Bispecific T-cell Engaging Antibodies for Cancer Therapy," *Cancer Res.* (2009) 69:4941-4944.)

The invention also includes a method for identifying suitable immunogens for use to generate antibodies by assessing the binding of the binding moieties of the invention, such as mAb's described above, to a candidate peptide or other molecule. This is an effective method, not only to identify suitable immunogens, but also to identify compounds that can be used as a basis for designing aptamers that mimic the binding moieties of the invention. The method is grounded in the fact that if a vaccine immunogen cannot bind to an optimally effective mAb, it is unlikely to be able to induce such antibodies. Conversely, an immunogen that is a faithful inverse of the optimal mAb provides a useful template for constructing a mimic of the optimal mAb. In its simplest form, this method employs a binding moiety such as one of the mAb's of the invention as an assay component and tests the ability of the binding moiety to bind to a candidate immunogen in a library of said candidates.

In addition, the ability of the binding moieties of the invention to overcome drug resistance in a variety of bacteria can be assessed by testing the binding moieties of the invention against a panel or library of DNABII proteins from a multiplicity of microbial species. Binding moieties that are able to bind effectively a multiplicity of such proteins are thus identified as suitable not only for dissolving biofilms in general, but also as effective against a variety of microbial strains. It is also useful to identify binding moieties that have utility in acidic environments wherein the affinity of a candidate binding moiety for a DNABII protein over a range of pH conditions is tested and moieties with a low nanomolar affinity at pH 4.5 are identified as having utility in acidic environments.

The binding moieties of the invention are also verified to have an affinity with respect to at least one DNABII protein greater than the affinity of a biofilm component for the DNABII protein which comprises comparing the affinity of the binding moiety for the DNABII protein versus the affinity of a component of the biofilm, typically branched DNA, for the DNABII protein. This can be done in a competitive assay, or the affinities can be determined independently.

The DNABII proteins used in these assays may be prepared in mammalian cells at relatively high yield.

All of the assays above involve assessing binding of two perspective binding partners in a variety of formats.

A multitude of assay types are available for assessing successful binding of two prospective binding partners. For example, one of the binding partners can be bound to a solid support and the other labeled with a radioactive substance, fluorescent substance or a colorimetric substance and the binding of the label to the solid support is tested after removing unbound label. The assay can, of course, work either way with the binding moiety attached to the solid support and a candidate immunogen or DNABII protein labeled or vice versa where the candidate is bound to solid support and the binding moiety is labeled. Alternatively, a complex could be detected by chromatographic means based on molecular weight such as SDS-page. The detectable label in the context of the binding assay can be added at any point. Thus, if, for example, the mAb or other binding moiety is attached to a solid support the candidate immunogen can be added and tested for binding by supplying a labeled component that is specific for the candidate immunogen. Hundreds of assay formats for detecting binding are known in the art, including, in the case where both components are proteins, the yeast two-hybrid assay.

In addition to this straightforward application of the utility of the binding moieties of the invention, the identification of a suitable powerful immunogen can be determined in a more sophisticated series of experiments wherein a panel of mAbs against the DNABII protein is obtained and ranked in order by efficacy. A full suite of antibodies or other binding moieties can be prepared against all possible epitopes by assessing whether additional binding moieties compete for binding with the previous panel of members. The epitopes for representative binding mAbs for each member of the complete suite can be accomplished by binding to a peptide array representing the possible overlapping epitopes of the immunogen or by X-ray crystallography, NMR or cryo-electron microscopy. An optimal vaccine antigen would retain the spatial and chemical properties of the optimal epitope defined as that recognized by the most efficacious mAbs as compared to less efficacious mAbs but does not necessarily need to be a linear peptide. It may contain non-natural amino acids or other crosslinking motifs.

Moreover, screening can include peptides selected based on their likelihood of being recognized by antibodies and based on their conservation across bacterial species. As described in Example 3 below, for IHF these two criteria have converged on a single peptide-residues 56-78 of *H. influenzae* and corresponding positions in other analogs.

Thus, even beyond the specific mAb's set forth herein, optimal immunogens can be obtained, which not only are useful in active vaccines, but also as targets for selecting aptamers. Specifically, in addition to positions 56-78 of *H. influenzae*, the peptides at positions 10-25 and 86-96 of *H. influenzae* are identified.

Another aspect of the invention is a method to prepare higher yields of the bacterial/microbial DNABII proteins which are typically somewhat toxic to bacteria. The standard method for preparation of these proteins is described by Nash, H. A., et al., J. Bacteriol (1987) 169:4124-4127 who showed that the IHF of *E. coli* could be effectively prepared if both chains of said protein (IHF alpha and IHF beta) are produced in the same transformant.

Applicants have found that they are able to obtain higher yields, as much as 5-10 mg/l of IHF, by producing both chains transiently in HEK293 cells. The expression of bacterial proteins that are toxic at high levels in bacteria is conveniently achieved in mammalian cells especially for those without glycosylation sites that would result in modification of the proteins when thus expressed. Purification of the resulting protein can be achieved using fast protein liquid chromatography (FPLC).

Applications

The binding moieties of the invention including antibodies are useful in therapy and prophylaxis for any subject that is susceptible to infection that results in a biofilm. Thus, various mammals, such as bovine, ovine and other mammalian subjects including horses and household pets and humans will benefit from the prophylactic and therapeutic use of these mAb's.

The binding moieties of the invention may be administered in a variety of ways. The peptides based on CDR regions of antibodies, including bispecific and single chain types or alternate scaffold types, may be administered directly as veterinary or pharmaceutical compositions with typical excipients. Liposomal compositions are particularly useful, as are compositions that comprise micelles or other nanoparticles of various types. Aptamers that behave as binding agents similar to mAb's can be administered in the same manner. Further, the binding agent may be conjugated to any of the solid supports known in the literature, such as PEG, agarose or a dextran, to function as an immunosorbent for extracting IHF from a biofilm. Alternatively, the peptide-based mAb's may be administered as the encoding nucleic acids either as naked RNA or DNA or as vector or as expression constructs. The vectors may be non-replicating viral vectors such as adenovirus vectors (AAV) or the nucleic acid sequence may be administered as mRNA packaged in a liposome or other lipid particle. Use of nucleic acids as drugs as opposed to their protein counterparts is helpful in controlling production costs.

These are administered in a variety of protocols, including intravenous, subcutaneous, intramuscular, topical (particularly for chronic non-healing wounds and periodontal disease), inhaled and oral or by suppository. Similar routes of administration can be used with regard to the binding moieties themselves. One useful way to administer the nucleic acid-based forms of either the binding moieties themselves (aptamers) or those encoding the protein form of binding moieties is through a needleless approach such as the agro-jet needle-free injector described in US2001/0171260.

The peptides that represent the epitopes of the IHF proteins as described herein are also useful as active components of vaccines to stimulate immunogenic responses which will generate antibodies in situ for disruption of biofilms. The types of administration of these immunogens or peptidyl mimetics that are similarly effective are similar to those for the administration of binding moieties, including various types of antibodies, etc. The peptidomimetics may themselves be in the form of aptamers or alternative structures that mimic the immunogenic peptides described herein. For those immunogens, however, that are proteins or peptides, the administration may be in the form of encoding nucleic acids in such form as will produce these proteins in situ. The formulation, routes of administration, and dosages are determined conventionally by the skilled artisan.

The types of conditions for which the administration either of the vaccine type for active generation of antibodies for biofilm control or for passive treatment by administering the antibodies per se, include any condition that is characterized by or associated with the formation of biofilms. These conditions include: heart valve endocarditis, both native and implanted (for which a substantial fraction of cases cannot be cured by high dose antibiotics due to the resistance associated with biofilm), chronic non-healing wounds (including venous ulcers and diabetic foot ulcers), ear and sinus infections, urinary tract infections, pulmonary infections (including subjects with cystic fibrosis or chronic obstructive pulmonary disease), catheter associated infections (including renal dialysis subjects), subjects with implanted prostheses (including hip and knee replacements), and periodontal disease.

As noted above, the binding moieties of the invention are not limited in their utility to therapeutic (or diagnostic) uses, but can be employed in any context where a biofilm is a problem, such as pipelines or other industrial settings. The mode of application of these binding moieties to the biofilms in these situations, again, is conventional.

The following examples are offered to illustrate but not to limit the invention.

Example 1

Preparation of Antibodies

Human peripheral antibody producing memory B cells were obtained from recovered sepsis patients or from anonymized blood bank donors, under informed consent. The cells were subjected to a CELLSPOT™ (Trellis Bioscience, Inc; Redwood City, CA) B-cell characterization and recovery assay to determine their ability to bind the DNABII protein derived from influenza virus (as described in U.S. Pat. Nos. 7,413,868 and 7,939,344). After isolating the B cells from whole blood, they were stimulated with cytokines and mitogens to initiate a brief period of proliferation and antibody secretion (lasting ~10 days) and plated for subjection to the assays; the encoding nucleic acids were extracted and used to produce the antibodies recombinantly.

Antibodies selected based on binding to at least one of the DNABII proteins or fragments thereof were characterized: TRL295, TRL1012, TRL1068, TRL1070, TRL1087, TRL1215, TRL1216, TRL1218, TRL1230, TRL1232, TRL1242 and TRL1245. Affinity was measured using a FORTEBIO OCTET™ (Sartorius, AG.; Goettingen, Germany) light interferometry biosensor to measure on and off rates (whose ratio yields the Kd). This result establishes the feasibility of a focused screen to isolate high affinity, cross-strain binding antibodies.

```
TRL295 heavy chain variable region has the amino acid sequence:
                                                         (SEQ ID NO: 1)
QVQLVESGGGLVQPGGSLRLSCAASGFPFSSYAMSWVRQAPGKGLEWVSAISGNGADSYY

ADSVKGRFTTSRDKSKNTVYLQMNRLRAEDTAVYYCAKDMRRYHYDSSGLHFWGQGTL

VTVSS;

TRL295 light chain variable region has the amino acid sequence:
                                                         (SEQ ID NO: 2)
DIELTQAPSVSVYPGQTARITCSGDALPKQYAYWYQQKPGQAPVVVIYKDSERPSGISERFS

GSSSGTTVTLTISGVQAGDEADYYCQSVDTSVSYYVVFGGGTKLTVL;

TRL1012 heavy chain variable region has the amino acid sequence:
                                                         (SEQ ID NO: 3)
QVQLVESGGGLVQPGGSLRLSCAASGFPFSSYAMSWVRQAPGKGLEWVSAISGNGADSYY

ADSVKGRFTTSRDKSKNTVYLQMNRLRAEDTAVYYCAKDMRRYHYDSSGLHFWGQGTL

VTVSS;

TRL1012 light chain variable region has the amino acid sequence:
                                                         (SEQ ID NO: 4)
DIMLTQPPSVSAAPGQKVTISCSGSSSNIGTNYVSWFQQVPGTAPKFLIYDNYKRPSETPDRF

SGSKSGTSATLDITGLQTGDEANYYCATWDSSLSAWVFGGGTKVTVL;

TRL1068 heavy chain variable region has the amino acid sequence:
                                                         (SEQ ID NO: 5)
QVQLVESGPGLVKPSETLSLTCRVSGDSNRPSYWSWIRQAPGKAMEWIGYVYDSGVTIYN

PSLKGRVTISLDTSKTRFSLKLTSVIAADTAVYYCARERFDRTSYKSWWGQGTQVTVSS;

TRL1068 light chain variable region has the amino acid sequence:
                                                         (SEQ ID NO: 6)
DIVLTQAPGTLSLSPGDRATLSCRASQRLGGTSLAWYQHRSGQAPRLILYGTSNRATDTPD

RFSGSGSGTDFVLTISSLEPEDFAVYYCQQYGSPPYTFGQGTTLDIK;
```

-continued

TRL1070 heavy chain variable region has the amino acid sequence:
(SEQ ID NO: 7)
QVQLVQSGGTLVQPGGSLRLSCAASGFTFSYYSMSWVRQAPGKGLEWVANIKHDGTERN

YVDSVKGRFTISRDNSEKSLYLQMNSLRAEDTAVYYCAKYYYGAGTNYPLKYWGQGTRV

TVSS;

TRL1070 light chain kappa variable region has the amino acid sequence:
(SEQ ID NO: 8)
DILMTQSPSSLSASVGDRVTITCRASQGIRNDLGWYQQKPGKAPKLLIYAASSLQSGVPSRF

SGSGSGTDFTLTISSLQPEDFATYYCLQDYNYPLTFGGGTKVEIKR;

TRL1087 heavy chain variable region has the amino acid sequence:
(SEQ ID NO: 9)
QVQLLESGPGLVRPSDTLSLTCTFSADLSTNAYWTWIRQPPGKGLEWIGYMSHSGGRDYNP

SFNRRVTISVDTSKNQVFLRLTSVTSADTAVYFCVREVGSYYDYWGQGILVTVSS;

TRL1087 light chain kappa variable region has the amino acid sequence:
(SEQ ID NO: 10)
DIEMTQSPSSLSASVGDRITITCRASQGISTWLAWYQQKPGKAPKSLIFSTSSLHSGVPSKFS

GSGSGTDFTLTITNLQPEDFATYYCQQKWETPYSFGQGTKLDMIR;

TRL1215 heavy chain variable region has the amino acid sequence:
(SEQ ID NO: 11)
QVQLVESGTEVKNPGASVKVSCTASGYKFDEYGVSWVRQSPGQGLEWMGWISVYNGKT

NYSQNFQGRLTLTTETSTDTAYMELTSLRPDDTAVYYCATDKNWFDPWGPGTLVTVSS;

TRL1215 light chain lambda variable region has the amino acid sequence:
(SEQ ID NO: 12)
DIVMTQSPSASGSPGQSITISCTGTNTDYNYVSWYQHHPGKAPKVIIYDVKKRPSGVPSRFS

GSRSGNTATLTVSGLQTEDEADYYCVSYADNNHYVFGSGTKVTVL;

TRL1216 heavy chain variable region has the amino acid sequence:
(SEQ ID NO: 13)
QVQLVESGGGVVQPGGSLRVSCAASAFSFRDYGIHWVRQAPGKGLQWVAVISHDGGKKF

YADSVRGRFTISRDNSENTLYLQMNSLRSDDTAVYYCARLVASCSGSTCTTQPAAFDIVVGP

GTLVTVSS;

TRL1216 light chain lambda variable region has the amino acid sequence:
(SEQ ID NO: 14)
DIMLTQPPSVSVSPGQTARITCSGDALPKKYTYWYQQKSGQAPVLLIYEDRKRPSEIPERFS

AFTSWTTATLTITGAQVRDEADYYCYSTDISGDIGVFGGGTKLTVL;

TRL1218 heavy chain variable region has the amino acid sequence:
(SEQ ID NO: 15)
QVQLLESGADMVQPGRSLRLSCAASGFNFRTYAMHWVRQAPGKGLEWVAVMSHDGYTK

YYSDSVRGQFTISRDNSKNTLYLQMNNLRPDDTAIYYCARGLTGLSVGFDYWGQGTLVTV

SS;

TRL1218 light chain lambda variable region has the amino acid sequence:
(SEQ ID NO: 16)
DIVLTQSASVSGSPGQSITISCTGTSSDVGGYNYVSWYQQHPGKAPKLMIYDVTTRPSGVSD

RFSGSKSGNTASLTISGLQAEDEADYYCSSYSSGSTPALFGGGTQLTVL;

TRL1230 heavy chain variable region has the amino acid sequence:
(SEQ ID NO: 17)
QVQLVQSGGGLVKPGGSLRLSCGASGFNLSSYSMNWVRQAPGKGLEWVSSISSRSSYIYY

ADSVQGRFTISRDNAKNSLYLQMNSLRAEDTAIYYCARVSPSTYYYYGMDVWGQGTTVT

VSS;

TRL1230 light chain lambda variable region has the amino acid sequence:
(SEQ ID NO: 18)
DIVLTQPSSVSVSPGQTARITCSGDELPKQYAYWYQQKPGQAPVLVIYKDNERPSGIPERFS

GSSSGTTVTLTISGVQAEDEADYYCQSADSSGTYVVFGGGTKLTVL;

-continued

TRL1232 heavy chain variable region has the amino acid sequence:
(SEQ ID NO: 19)
QVQLVESGAEVKKPGALVKVSCKASGYTFSGYYMHWVRQAPGQGLEWMGWINPKSGGT

KYAQKFQGRVTMTRDTSISTAYMELSRLRSDDTAVYFCARGGPSNLERFLERLQPRYSYD

DKYAMDVWGQGTTVTVSS;

TRL1232 light chain kappa variable region has the amino acid sequence:
(SEQ ID NO: 20)
DIVMTQSPGTLSLSPGARATLSCRASQSVSSIYLAWYQQKPGQAPRLLIFGASSRATGIPDRF

SGSGSGTDFTLTISRLEPEDFAVYYCQQYGSSPYTFGQGTKLEIKR;

TRL1242 heavy chain variable region has the amino acid sequence:
(SEQ ID NO: 21)
QVQLVQSGTEVKKPGESLKISCEGSRYNFARYWIGWVRQMPGKGLDWMGITYPGDSDTRY

SPSFQGQVSISADKSISTAYLQWNSLKASDTAMYYCARLGSELGVVSDYYFDSWGQGTLV

TVSS;

TRL1242 light chain kappa variable region has the amino acid sequence:
(SEQ ID NO: 22)
DIVLTQSPDSLAVSLGERATINCKSSQSVLDRSNNKNCVAWYQQKPGQPPKWYRAATRE SGVPDRFSGSGSGTDFSLTISSLQAEDVAVYFCQQYYSIPNTFGQGTKLEIKR;
and TRL1245 heavy chain variable region has the amino acid sequence:
(SEQ ID NO: 23)
QVQLVESGGGLVKAGGSLRLSCVASGFTFSDYYMSWIRQAPGKGLEWISFISSSGDTIFYAD

SVKGRFTVSRDSAKNSLYLQMNSLKVEDTAVYYCARKGVSDEELLRFWGQGTLVTVSS;

TRL1245 light chain variable region has the amino acid sequence:
(SEQ ID NO: 24)
DIVLTQDPSVSVSPGQTARITCSGDALPKKYAYWYQQKSGQAPVLVIYEDTKRPSGIPERFS

GSSSGTVATLTISGAQVEDEADYYCYSTDSSGNQRVFGGGTKLTVL.

The encoding nucleotide sequences for the variable regions of TRL295 are:

Heavy Chain:
(SEQ ID NO: 25)
caggtgcagctggtgcagtctgggggaggcttggtacagcctggggggtc cctgagactctcctgtgcagcctctggatttaccttcagtgattatagta tgaactgggtccgccaggctccagggaagggactggaatggctttcatac attagtcacactattactaccatatactacgccgactctgtgaagggccg attcaccatctccagagacaatgccgacagctcactgtatctccaaatga acagcctgggagacgaggacacggctgtgtattactgtgcgagagctcca ttagtaaactgtagtactagtggctgccagtccggaagctggttcgacac ctggggccagggaaccctggtcaccgtctcctca;

Light Chain:
(SEQ ID NO: 26)
atatcgagctgactcaggcaccctcggtgtcagtgtatccaggacagacg gccaggatcacctgctctggagatgcactgccaaagcaatatgcttattg gtaccagcagaagccaggccaggcccctgtggtggtgatatataaagaca gtgagaggccctcagggatctctgagcgattctctggctccagctcgggg acaacagtcacgttgaccatcagtggagtccaggcagggacgaggctga ctattattgtcaatcagttgacaccagtgtttcttattatgtggtcttcg gcggagggaccaagttgaccgtccta.

The encoding nucleotide sequences for the variable regions of TRL1012 are:

Heavy Chain:
(SEQ ID NO: 27)
caggtgcagctggtggagtccggggaggcttggtacagcctggggggtc cctgagactttcctgtgccgcctctggattccccttcagtagttatgcca tgagttgggtccgtcaggctccagggaaggggctggagtgggtctcagcc atcagtggcaacggcgctgactcatattacgcagactccgtgaagggccg cttcaccacttccagagacaagtccaagaatacagtttatttgcaaatga acagactcagggccgaggacacggccgtatattactgtgcgaaagatatg cgacggtatcattatgacagtagtggtctgcacttctggggccagggaac cctggtcaccgtctcctca;

Light Chain:
(SEQ ID NO: 28)
gatatcatgctgactcagccccctcagtgtctgcggccccggacagaa ggtcaccatctcctgctctggaagcagctccaacattgggacgaattatg tgtcctggaccagcaggtcccaggaacagccccaaattcctcatttatg acaattataaacgaccctcagaaactcctgaccgattctctggctccaag tctggcacgtcggccaccctggacatcaccggactccagactggggacga ggccaattattactgcgcaacatgggacagtagcctgagtgcttgggtgt tcggcggagggaccaaggtgaccgtcctg.

The encoding nucleotide sequences for the variable regions of TRL1068 are:

Heavy Chain:
(SEQ ID NO: 29)
caggtgcagctggtggagtccggcccaggactggtgaagccttcggagac cctgtccctcacctgcagggtctctggtgactccaatcggccttcctact ggagctggatcaggcaggcccagggaaggcaatggagtggataggttat gtctatgacagtggggtcaccatctacaatccctccctcaagggtcgagt cacaatatcactagacacgtcgaagacgcggttctccctgaaactgacct ctgtgatcgctgcggacacggccgtatattattgtgcgcgagaacgattg atcggacatcgtataagagttggtggggcagggaacgcaggtcaccgtc tcctca;

Light Chain:
(SEQ ID NO: 30)
gatatcgtgctgactcaggccccaggcactctgtattgtctccaggggac agagccaccctctcctgtagggccagtcagcgtcttggcggcacgtcctt agcctggtaccagcacagatctggccaggctcccaggctcatcctctacg gaacttcaaacagggccactgacacccctgacaggtttagtggcagtggg tctgggacagacttcgttctcaccatcagttccctggagcctgaagattt tgcagtgtattactgtcagcaatatggcagcccaccgtacacttttggcc aggggaccactctggacatcaaa.

The encoding nucleotide sequences for the variable regions of TRL1070 are:

Heavy Chain:
(SEQ ID NO: 31)
caggtgcagctggtgcagtctgggggaaccttggtccagccggggggtc cctgagactctcctgtgcagcctctggattcacctttagttactactcga tgagctgggtccgccaggctccagggaaggggctggagtgggtggccaac ataaagcacgatggaactgagagaaattatgtggactctgtgaagggccg attcaccatctccagagacaacagcgagaagtctctttacctgcaaatga acagcctgagagccgaggacacggctgtgtattactgtgcgaagtattat tatggtgccgggactaattatccccttaagtactggggccagggaacccg ggtcaccgtctcctca;

Light Chain:
(SEQ ID NO: 32)
gatatcctgatgacccagtctccatcctccctgtctgcatctgtaggaga cagagtcaccatcacttgccgggcaagtcagggcattagaaatgatttag gctggtatcagcagaaaccagggaaagcccctaagctcctgatctatgct gcatccagtttacaaagtggggtcccatcaaggttcagcggcagtggatc tggcacagatttcactctcaccatcagcagcctgcagcctgaagattttg caacttattactgtctacaagattacaattacccgctcactttcggcgga gggaccaaggtggagatcaaacga.

The encoding nucleotide sequences for the variable regions of TRL1087 are:

Heavy Chain:
(SEQ ID NO: 33)
caggtgcagctgctcgagtcaggcccaggcctggttaggccctcggacac cctgtccctcacctgcacttttccgctgacctcagcaccaacgcctatt ggacctggatccggcagccccaggaaagggactggagtggattggctat atgtctcatagtggggaagggattacaatccctccttcaaccggcgagt caccatttcagtggacacgtcgaagaaccaggttttcttgaggctgacgt cagtgacctctgcggacacggccgtctatttctgtgtgagagaagtcggc agttactacgactactggggccagggaatcctggtcaccgtctcctca;

Light Chain:
(SEQ ID NO: 34)
gatatcgagatgacccagtctccatcctctttgtctgcatctgtcggaga cagaatcaccatcacttgtcgggcgagtcagggtattagcacctggttag cctggtatcagcagaaaccggggaaagcccctaagtccctgatcttttct acgtccagcctgcatagtggggtcccctcaaagttcagcggcagtgggtc tgggacagacttcactctcaccatcaccaacctgcagcctgaagattttg caacttattactgccaacagaaatgggagaccccttatagttttggccag gggaccaagctggacatgatacga.

The encoding nucleotide sequences for the variable regions of TRL1215 are:

Heavy Chain:
(SEQ ID NO: 35)
caggtgcagctggtggagtctggaactgaggtgaagaaccctggagcctc agtgaaggtctcctgcacggcctctggttacaaatttgacgaatatggtg tcagttgggtgcgacagtccctggacaaggacttgagtggatgggatgg atcagtgtttataatggcaagacaaactatagccagaactttcagggcag actcaccctgaccacagagacatccaccgacacagcctacatggagctta cgagcctcagacctgacgacacggccgtctattactgtgcgacagacaaa aactggttcgaccctggggcccgggaaccctggtcaccgtctcctca;

Light Chain:
(SEQ ID NO: 36)
gatatcgtgatgacccagtctccctccgcgtccgggtctcctggacagtc aatcaccatctcctgcactggaaccaacactgattataattatgatcctg gtaccagcaccaccccggcaaagcccccaaagtcattatttatgacgtca aaaagcggcctcgggggtccctagtcgcttctctggctccaggtctggc aacacggccaccctgaccgtctctgggctccagactgaggatgaggctga ttattattgtgtctcatatgcagacaacaatcattatgtcttcggaagtg ggaccaaggtcaccgtcctg.

The encoding nucleotide sequences for the variable regions of TRL1216 are:

Heavy Chain:
(SEQ ID NO: 37)
caggtgcagctggtggagtccggggggaggcgtggtccagcctggagggtc cctgagagtctcctgtgcagcctctgcgttcagtttcagggattatggca tacactgggtccgccaggctccaggcaaggggctgcaatgggtggcggtt -continued atttcacatgatggaggtaagaaattctatgcagactccgtgagggccg attcaccatctccagagacaattccgagaacacactgtatctccaaatga acagcctgagatctgacgacacggctgtctattactgtgcgaggctcgtt gccagttgcagtggttccacctgcacaacgcaacctgctgcctttgacat ttggggcccagggacattggtcaccgtctcttca;

Light Chain:
(SEQ ID NO: 38)
gatatcatgctgactcagccgcctcggtgtcagtgtccccaggacaaac ggccaggatcacctgctctggagatgcattgccaaaaaaatatacttatt ggtatcagcagaagtcaggccaggcccctgttctgctcatctatgaggac aggaaacgaccctccgagatccctgagagattctctgccttcacctcatg gacgacggccaccttgactatcactggggcccaggtgagagatgaagctg actactactgttattcaacagacatcagtggtgatataggagtgttcggc ggagggaccaagctgaccgtccta.

The encoding nucleotide sequences for the variable regions of TRL1218 are:

Heavy Chain:
(SEQ ID NO: 39)
gatatcgtgctgactcagtcggcctccgtgtctgggtctcctggacagtc gatcaccatctcctgcactggaaccagcagtgacgttggtggatataact atgtctcctggtaccaacaacacccaggcaaagcccccaaactcatgatt tatgatgtcactactcggccttcaggggtttctgatcgcttctctggctc caagtctggcaacacggcctccctgaccatctctgggctgcaggctgagg acgaggctgattattattgcagctcatattcaagcggctccacacctgct ctgtttggggggggcacccagctgaccgtcctc;

Light Chain:
(SEQ ID NO: 40)
gatatcgtgctgactcagtcggcctccgtgtctgggtctcctggacagtc gatcaccatctcctgcactggaaccagcagtgacgttggtggatataact atgtctcctggtaccaacaacacccaggcaaagcccccaaactcatgatt tatgatgtcactactcggccttcaggggtttctgatcgcttctctggctc caagtctggcaacacggcctccctgaccatctctgggctgcaggctgagg acgaggctgattattattgcagctcatattcaagcggctccacacctgct ctgtttggggggggcacccagctgaccgtcctc.

The encoding nucleotide sequences for the variable regions of TRL1230 are:

Heavy Chain:
(SEQ ID NO: 41)
caggtgcagctggtgcagtctggggaggcctggtcaagcctggggggtc cctgagactctcctgtggagcctctggatttaacctcagtagttatagca tgaactgggtccgccaggctccaggaaggggctggagtgggtctcatcc attagtagtagaagtagttacatatactatgcagactcagtgcagggccg attcaccatctccagagacaacgccaagaactcactgtatctgcaaatga acagcctgagagccgaggacacggctatatattactgtgcgagagtatct ccgtccacctattattattatggtatggacgtctggggccaagggaccac ggtcaccgtctcctca;

Light Chain:
(SEQ ID NO: 42)
gatatcgtactcactcagccgtcctcggtgtcagtgtccccaggacagac ggccaggatcacctgctctggagatgaattgccaaagcaatatgcttatt ggtaccagcagaagccaggccaggcccctgtgttggtaatatataaagac aatgagaggccctcagggatccctgagcgattctctggctccagctcagg gacaacagtcacgttgaccatcagtgagtccaggcagaagacgaggctg actattactgtcaatcagcagacagtagtggtacttatgtggtgttcggc ggagggaccaagctgaccgtccta.

The encoding nucleotide sequences for the variable regions of TRL1232 are:

Heavy Chain:
(SEQ ID NO: 43)
caggtgcagctggtggagtctggggctgaggtgaagaagcctggggcctt agtgaaggtctcctgcaaggcttctggatacaccttcagcggctactata tgcactgggtgcgacaggcccctggacaagggcttgagtggatgggatgg atcaacccta agagtggtggcacaaagtatgcacagaagtttcagggccg ggtcaccatgaccagggacacgtccatcagcacagcctacatggagttga gcaggctaagatctgacgacacggccgtgtatttctgtgcgagaggcgga ccttcaaatttggaacgattatggagaggttacaacccgctacagttac gacgacaagtatgctatggacgtctggggccaagggaccacggtcaccgt ctcctca;

Light Chain:
(SEQ ID NO: 44)
gatatcgtgatgacccagtctccaggcaccctgtctttgtctccagggc aagagccaccctctcctgcagggccagtcagagtgttagcagcatctatt tagcctggtaccagcagaaacctggccaggctcccaggctcctcatcttt ggtgcatccagcagggccactggcatcccagacaggttcagtggcagtgg gtctgggacagacttcactctcaccatcagcagactggagcctgaagatt ttgcagtgtattactgtcagcagtatggtagctcaccgtacacttttggc caggggaccaagctggagatcaaacgaa.

The encoding nucleotide sequences for the variable regions of TRL1242 are:

Heavy Chain:
(SEQ ID NO: 45)
caggtgcagctggtgcagtctggaacagaagtgaaaaagcccggggagtc tctgaagatctcctgtgagggttctcgatacaactttgccaggtactgga tcggctgggtcgccagatgcccggaaaaggcctggactggatgggggatc atctatcctggtgactccgataccagatacagcccgtccttccaaggcca ggtcagcatctcagccgacaagtccatcagtaccgcctacctgcagtgga acagcctgaaggcctcggacaccgccatgtattattgtgcgagacttggg -continued

```
agcgagcttggagtggtctctgattattactttgactcctggggccaggg aaccctggtcaccgtctcctca;

Light Chain:
                                          (SEQ ID NO: 46)
gatatcgtgagactcagtctccagactccctggctgtgtctctgggcgag agggccaccatcaactgcaagtccagccagagtgttttagacaggtccaa caataagaactgtgtagcttggtaccagcagaaaccgggacagcctccta aactgctcatttaccgggctgctacccgggaatccggggtccctgatcga ttcagtggcagcgggtctgggacagacttcagtctcaccatcagcagcct gcaggctgaagatgtggcagtttatttctgtcagcaatattatagtattc cgaacacttttggccaggggaccaagctggagatcaaacga.
```

The encoding nucleotide sequences for the variable regions of TRL1245 are:

```
Heavy Chain:
                                          (SEQ ID NO: 47)
caggtgcagctggtggagtctgggggaggcttggtcaaggctggagggtc cctgagactctcctgtgtagcctctggattcaccttcagcgactactaca tgtcctggattcgccaggctccagggaaggggctggagtggatttcattt attagtagtagtggtgataccatattttacgcagactctgtgaagggccg attcaccgtctccagggacagcgccaagaactcactgtatcttcaaatga acagcctgaaagtcgaggacacggccgtgtattactgtgcgaggaagggg gtgtccgacgaggaactactgcgcnctggggccagggaaccctggtcacc gtctcctca;

Light Chain:
                                          (SEQ ID NO: 48)
gatatcgtgctgactcaggacccctcggtgtcagtgtccccaggacaaac ggccaggatcacctgctctggagatgcattgccaaaaaaatatgcttatt ggtaccagcagaagtcaggccaggccctgtgctggtcatctatgaggac accaaacgaccctccgggatccctgagagattctctggctccagctcagg gacagtggccaccttgactatcagtggggcccaggtggaggatgaagctg actactattgttactcaacagacagcagcggtaatcagagggtattcggc ggagggaccaagctgaccgtccta.
```

Example 2

Determination of Affinity

For practice of the assay method, ~1 mg of IHF was required. IHF is difficult to express in bacteria (since it has a dual function involving gene regulation, leading to toxicity to bacteria expressing high levels). Obtaining sufficient material for mAb discovery from bacterial sources is thus difficult (and expensive). The protein was therefore expressed in HEK293 (mammalian) cells, with a poly-histidine tag to enable easy purification. The homologs from *Staphylococcus aureus* (Sa), *Pseudomonas aeruginosa* (Pa), *Klebsiella pneumoniae* (KP) and *Haemophilus influenzae* (Hi) were all prepared in this manner. These four are of particular utility since they span a substantial portion of the diversity in sequences of the DNABII family.

TRL295 was shown to bind with high affinity to the IHF peptide of *H. influenzae* and moreover to bind to IHF from additional bacterial species.

The chart below shows the degree of identity to *Haemophilus* of various IHF and HU proteins from a variety of bacterial species.

| Species | Protein | Sequence Identity to Haemophilus |
|---|---|---|
| Haemophilus influenzae | IHF alpha | 100 |
| Escherichia coli | IHF alpha | 67 |
| Enterobacter cloacae | IHF alpha | 66 |
| Enterobacter aerogenes | IHF alpha | 66 |
| Klebsiella oxytoca | IHF alpha | 65 |
| Pseudomonas aeruginosa | IHF alpha | 61 |
| Acinetobacter baumannii | IHF alpha | 58 |
| Streptococcus pneumoniae | HU | 38 |
| Staphylococcus aureus | HU | 38 |

Further, the high affinity binding of TRL295 was shown to be retained even as the pH was decreased from physiological (pH 7.5) to pH 4.5, as shown below.

| pH | Kd (nM) |
|---|---|
| 7.5 | 4.2 |
| 6.5 | 2.8 |
| 5.5 | 2.8 |
| 4.5 | 3.7 |
| 3.5 | no binding |
| 2.5 | no binding |

This is important since bacteria often secrete lactic acid which reduces the local micro-environment pH as a way of inhibiting immune system attack.

The chart below shows the results of ELISA assays to determine binding of various DNABII proteins. The numbers represent OD values which are useful for comparison to TRL1068—higher values represent higher binding affinity. TRL1068 shows similar binding to all four homologs, but low binding to BSA, as does TRL1215. The abbreviations are

| mAb# | BSA | IHF (Hi) | IHF (Kp) | IHF (Pa) | IHF (Sa) |
|---|---|---|---|---|---|
| 1070 | 0.08 | 0.11 | 0.5 | 0.13 | 0.3 |
| 1087 | 0.05 | 0.06 | 0.06 | 0.06 | 0.14 |
| 1068 | 0.18 | 1.61 | 1.55 | 1.57 | 1.55 |
| 1215 | 0.05 | 1.9 | 1.6 | 1.7 | 1.4 |
| 1216 | 0.05 | 0.06 | 0.4 | 0.7 | 0.5 |
| 1068 | 0.05 | 1.9 | 3.1 | 3.1 | 3 |
| 1218 | 0.04 | 0.04 | 0.06 | 0.09 | 1 |
| 1068 | 0.04 | 0.2 | 2.1 | 2.1 | 2.1 |
| 1230 | 0.05 | 0.06 | 0.07 | 0.3 | 0.1 |
| 1232 | 0.07 | 0.1 | 0.1 | 0.2 | 0.2 |
| 1068 | 0.08 | 2 | 3.1 | 3.2 | 3 |

The affinity of TRL1068 for the target protein was directly determined using a FORTEBIO OCTET™ (Sartorius, AG.; Goettingen, Germany) light interferometry biosensor with Kd determined by standard methods for measuring ratio of on and off rates (Ho D, et al., BioPharm International (2013) 48-51). The values were: 1 nM for *Staphylococcus aureus* (Sa), 1 nM for *Pseudomonas aeruginosa* (Pa), 7 nM for *Klebsiella pneumoniae* (Kp) and 350 nM for *Haemophilus influenzae* (Hi).

Example 3

Epitope Selection for Focused mAb Discovery

Figure 1B:
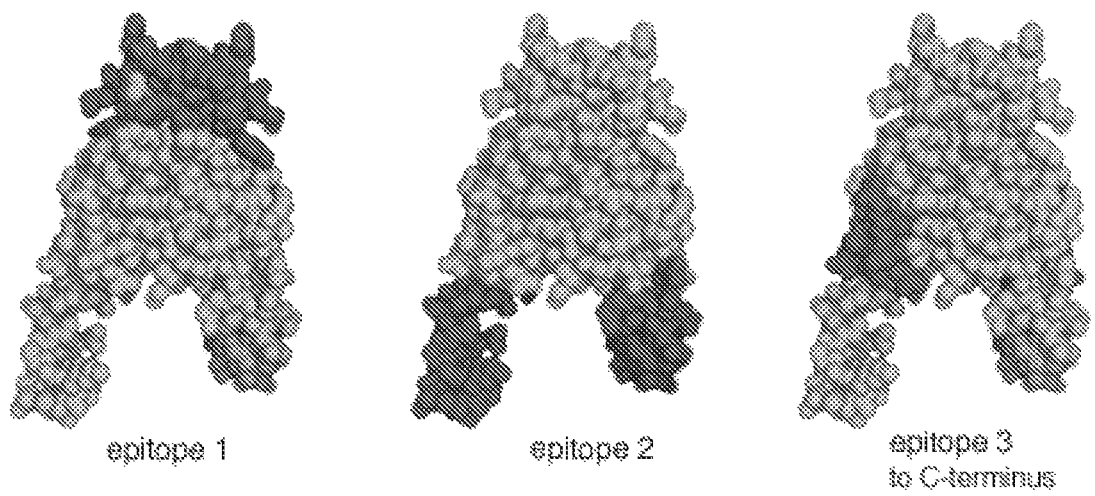
FIG. 1B shows these likely antigenic sites mapped onto the crystal structure of the IHF protein (based on the Protein Data Bank (pdb) structure designated 1OWF).

Computational methods for analyzing the likelihood of antigenicity (induction of antibody responses) are known in the art (reviewed by J. Ponomarenko, et al., in BMC Bioinformatics (2008) 9:514). Using an improved variation of these published methods, a map of the likely epitopes was generated for the IHF from *Haemophilus influenzae* from a model of the structure based on the published structure found in the Protein Data Bank (pdb 1OWF) (FIG. 1B). For the display in FIG. 1A, a value was assigned to the residue at the midpoint of each 11-amino acid segment. A value above 0.9 denotes a region with high likelihood of being susceptible to antibody binding.

Three regions were identified as having high likelihood of being recognized by antibodies: residues 10-25, 56-78, and 86-96.

Figure 2:
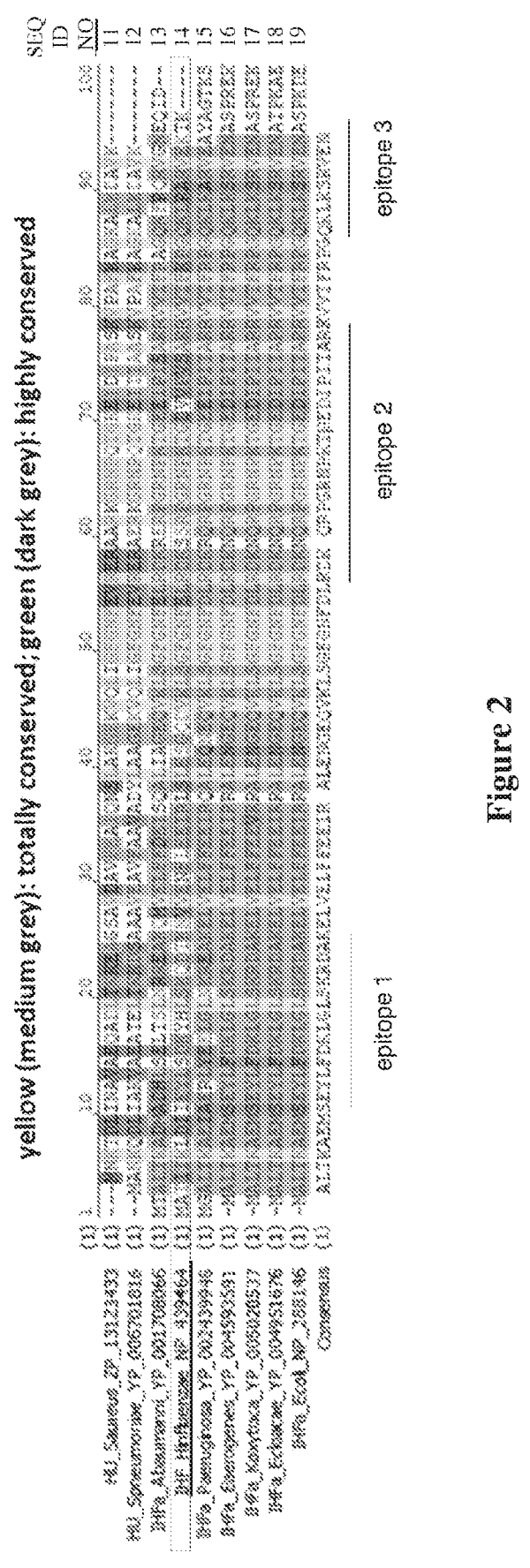

As illustrated in FIG. 2, the region from residues 56-78 of the IHF protein is substantially conserved across multiple clinically important bacterial species. Structural modeling of IHF from multiple species has confirmed that the homology is high, particularly in the DNA binding region (Swinger, K. K., et al., Current Opinion in Structural Biology (2004) 14:28-35). Peptides that only partially overlap with this optimal region are less likely to fold spontaneously into the relevant three dimensional conformation and will be more difficult to chemically crosslink in order to lock in that conformation. Optimizing the fidelity to the native protein in this manner is advantageous for both mAb discovery and for use of the peptide as an immunogen.

As noted above, the epitopes thus identified are positions 10-25 of *H. influenzae* IHF: IEYLSDKYHLSKQDTK (SEQ ID NO:49); positions 56-78 of *H. influenzae* IHF: RDKSSRPGRNPKTGDVVAASARR (SEQ ID NO:50); and positions 86-96 of *H. influenzae* IHF: QKLRARVEKTK (SEQ ID NO:51).

Figure 3A:
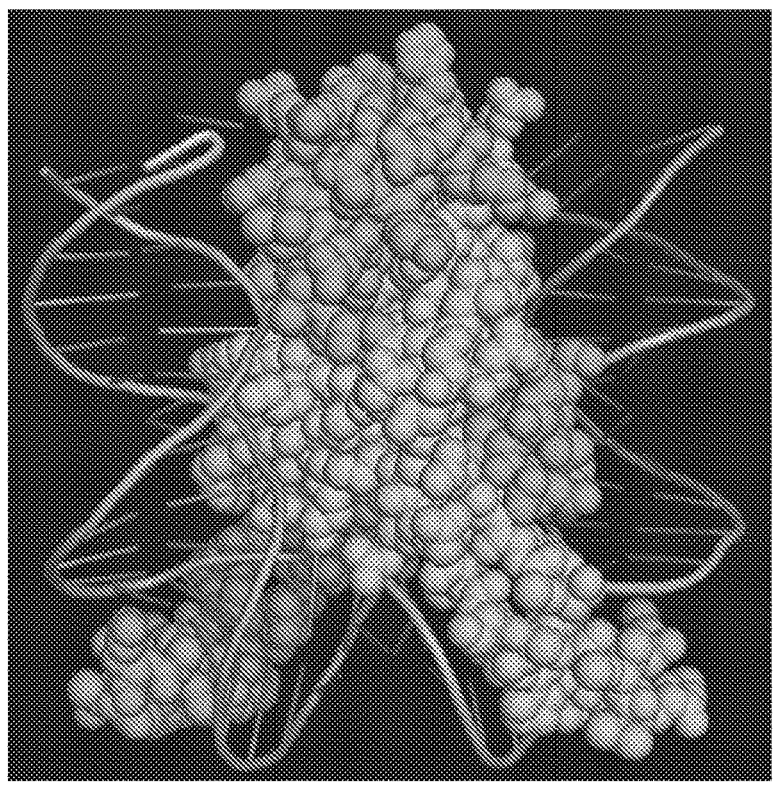
FIG. 3A shows a three-dimensional model of IHF proteins in their native dimeric form as complexed with DNA.
Figure 3B:
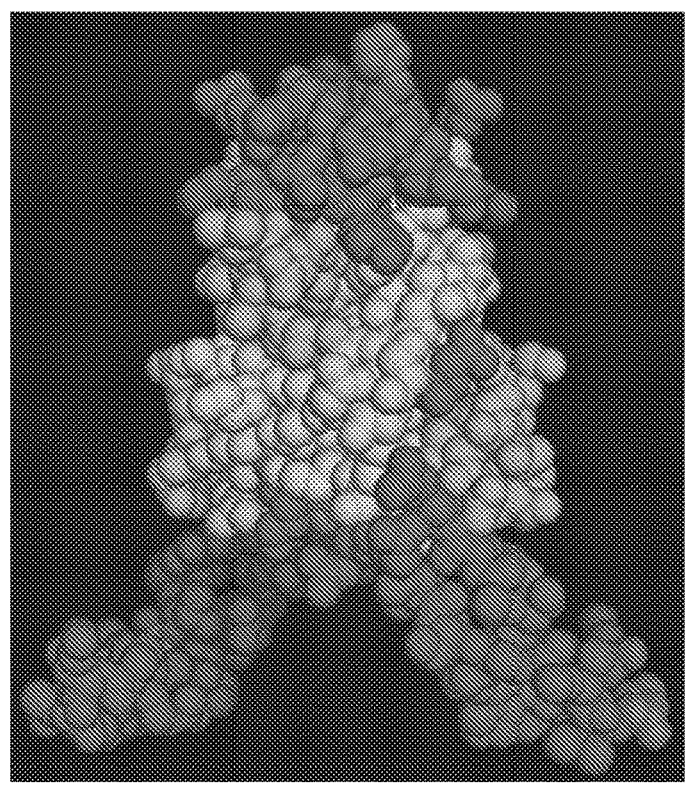
FIG. 3B shows the predicted highly antigenic regions (the darkened regions shown (which are red in the color version). The epitopes 2 and 3 identified in FIG. 1 are partially shielded from exposure to the immune system by DNA which is abundant in the biofilm.

FIG. 3A shows a computational construction of the IHF dimer complexed with DNA. The B cell epitopes of the invention are shown in FIG. 3B. FIG. 3A shows that the epitopes are partially masked by DNA when bound. However, if exposed, these portions of the proteins may generate antibodies of high affinity capable of binding them and thus preventing the formation of biofilm or causing an established biofilm to lose structural integrity as the DNABII protein is sequestered by the antibody. Other sites on the DNABII protein may also suffice to achieve extraction of the protein out of the biofilm based on higher affinity binding by the mAb as compared to the protein's affinity for components of the biofilm.

Example 4

In Vitro Bioactivity Assessment

Figure 4A:
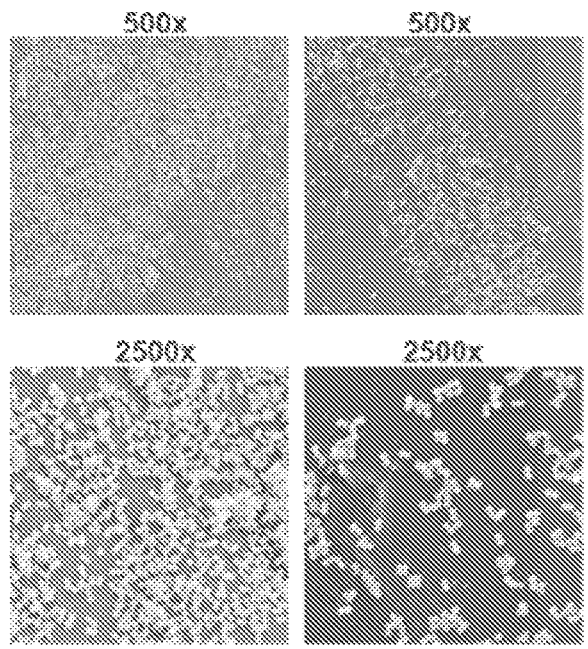
FIG. 4A shows *Staphylococcus aureus* (Sa) biofilm treated for 12 hours with an isotype control mAb that does not bind the target protein (growth control) or with TRL1068 at 1.2 g/mL (~10 nM), a native human mAb against a conserved epitope on DNABII proteins. TRL1068 caused dissolution of the biofilm, as evident at both low (500×) and high (2500×) magnification (scanning electron microscope images).
Figure 4B:
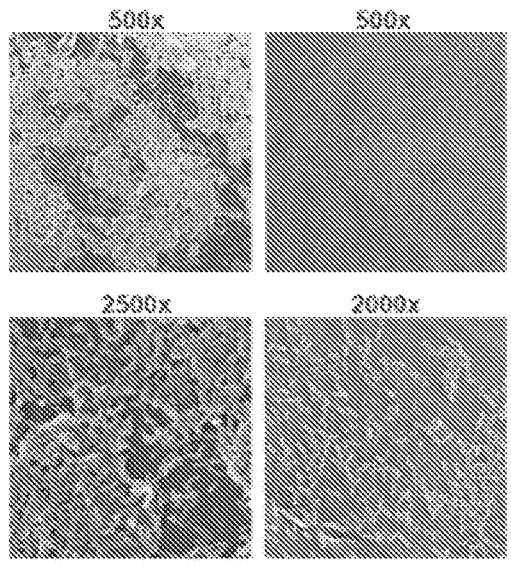
FIG. 4B shows the parallel experiment on *Pseudomonas aeruginosa* (Pa) biofilm.

TRL1068 was tested for bioactivity using a commercial assay from Innovotech (Edmonton, Alberta; Canada). Biofilms were formed in multiple replicates on pins in a 96-well microplate format exposed to media including *Pseudomonas aeruginosa* (ATCC 27853) or *Staphylococcus aureus* (ATCC 29213). Following biofilm formation, the pins were treated in different wells with a non-immune isotype control mAb or with TRL1068 at 1.2 μg/mL (~10 nM) for 12 hours. As evident in the scanning electron micrographs of the treated surfaces in FIG. 4, TRL1068 was highly effective at dissolving the biofilm. These results establish that the mAb can degrade the biofilm, thereby removing the attached bacteria.

Example 5

In Vivo Bioactivity Assessments

Several animal models exist for evaluation of activity. For example, at University Hospital Basel (Switzerland), a model for biofilm on implanted prostheses involves implanting polytetrafluoroethylene tissue cages (Angst+Pfister; Zurich, Switzerland) subcutaneously in BALB/c mice, which are then allowed to heal for 2 weeks. After confirming sterility of the cage by extracting fluid from it, the site is infected with $4\times10^3$ CFU (colony-forming units) of *S. aureus* (ATCC 35556), an inoculum mimicking a perioperative infection. After 24 hours, the site is injected with drug. After 72 hours, the mice are sacrificed and the tissue cage recovered. Viable bacteria are counted by plating on blood agar (Nowakowska J., et al., Antimicrob Agents Chemother (2013) 57:333).

A second example is a model that involves inducing biofilm on heart valves, mimicking native valve endocarditis (Tattevin P., et al., Antimicrob Agents Chemother (2013) 57:1157). New Zealand white rabbits are anesthetized. The right carotid artery is cut and a polyethylene catheter is positioned across the aortic valve and secured in place. Twenty four hours later, 1 mL of saline plus $8\times10^7$ CFU of *S. aureus* is injected through the catheter, which induces a biofilm infection in 95% of the animals. Drugs (anti-biofilm and antibiotic) are administered i.v. and efficacy is evaluated after 4 days by tissue pathology and blood bacterial levels.

---

The invention claimed is:

1. A monoclonal antibody (mAb) or antigen binding fragment thereof that specifically binds a DNA binding protein II (DNABII), wherein the mAb or antigen binding fragment thereof comprises:

a heavy chain variable region (SEQ ID NO:1) and a light chain variable region (SEQ ID NO: 2) of TRL1068;

a heavy chain variable region (SEQ ID NO:21) and a light chain variable region (SEQ ID NO: 22) of TRL1330; or, a heavy chain variable region (SEQ ID NO:25) and a light chain variable region (SEQ ID NO: 26) of TRL1337.

2. The mAb or antigen binding fragment thereof of claim 1, wherein mAb is an Fv antibody, a bispecific antibody, a chimeric antibody, or antigen binding fragment thereof.

3. The mAb or antigen binding fragment thereof of claim 1, wherein the mAb is a complete antibody.

4. The mAb or antigen binding fragment thereof of claim 3, wherein the complete antibody comprises generic constant regions heterologous to the variable regions thereof.

5. The mAb or antigen binding fragment thereof of claim 1, wherein the mAb or antigen binding fragment thereof has an affinity for the DNANH-DNABIL protein that exceeds an affinity of the DNABII protein for a component of a biofilm that includes the DNABII protein.

6. The mAb or antigen binding fragment thereof of claim 1, wherein the mAb or antigen binding fragment thereof binds a DNABII protein from at least three different bacterial species.

7. The mAb or antigen binding fragment thereof of claim 3, wherein the mAb or antigen binding fragment thereof (i) has an affinity for the DNABII protein that exceeds an affinity of the DNABII protein for a component of a biofilm that includes the DNABII protein and (ii) binds DNABII protein from at least three different bacterial species.

8. A pharmaceutical or veterinary composition which comprises as an active ingredient the mAb or antigen binding fragment thereof of claim 1 and a suitable pharmaceutical excipient.

9. The pharmaceutical or veterinary composition of claim 8, further comprising at least one antibiotic and at least one additional active ingredient, the active ingredient comprising an immunostimulant, an antipyrogenic, or an analgesic.

10. A monoclonal antibody (mAb) that specifically binds a DNA binding protein II (DNABII), the antibody comprising:
a heavy chain variable region of (SEQ ID NO:1) and a light chain variable region (SEQ ID NO: 2) of TRL1068;
a heavy chain variable region of (SEQ ID NO:21) and a light chain variable region (SEQ ID NO: 22) of TRL1330; or,
a heavy chain variable region of (SEQ ID NO:25) and a light chain variable region (SEQ ID NO: 26) of TRL1337; and
wherein the mAb is an Fv antibody, a bispecific antibody, a chimeric antibody, or a complete antibody and wherein the complete antibody comprises generic constant regions heterologous to the variable regions thereof.

11. The mAb of claim 10, wherein the mAb binds a DNABII protein from at least three different bacterial species.

12. A pharmaceutical or veterinary composition which comprises as an active ingredient the mAb of claim 10 and a suitable pharmaceutical excipient.

13. The pharmaceutical or veterinary composition of claim 12, further comprising at least one antibiotic and at least one additional active ingredient, the active ingredient comprising an immunostimulant, an antipyrogenic, or an analgesic.

14. A monoclonal antibody (mAb) that specifically binds a DNA binding protein II (DNABII), wherein (i) the mAb is an Fv antibody, a bispecific antibody, a chimeric antibody, or a complete antibody, wherein (ii) the mAb comprises a heavy chain variable region of (SEQ ID NO:1) and a light chain variable region (SEQ ID NO: 2) of TRL1068, and wherein (iii) the complete antibody comprises generic constant regions heterologous to the variable regions thereof.

15. The mAb of claim 14, wherein the mAb binds DNABII protein from at least three different bacterial species.

16. The mAb of claim 14, wherein the mAb or antigen binding fragment thereof has an affinity for the DNABII protein that exceeds an affinity of the DNABII protein for a component of a biofilm that includes the DNABII protein.

17. A pharmaceutical or veterinary composition which comprises as an active ingredient the mAb of claim 14 and a suitable pharmaceutical excipient.

18. The pharmaceutical or veterinary composition of claim 17, further comprising at least one antibiotic and at least one additional active ingredient, the active ingredient comprising an immunostimulant, an antipyrogenic, or an analgesic.

* * * * *

SEQUENCE LISTING

<160> NUMBER OF SEQ ID NOS: 51

<210> SEQ ID NO 1
<211> LENGTH: 123
<212> TYPE: PRT
<213> ORGANISM: Homo sapiens

<400> SEQUENCE: 1

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Asn Gly Asp Ser Tyr Tyr Ala Asp Ser Val
 50                  55                  60

Lys Gly Arg Phe Thr Thr Ser Arg Asp Lys Ser Lys Asn Thr Val Tyr
 65                  70                  75                  80

Leu Gln Met Asn Arg Leu Arg Ala Glu Asp Thr Ala Val Tyr Tyr Cys
                 85                  90                  95

Ala Lys Asp Met Arg Arg Tyr His Tyr Asp Ser Ser Gly Leu His Phe
                100                 105                 110

Trp Gly Gln Gly Thr Leu Val Thr Val Ser Ser
            115                 120

<210> SEQ ID NO 2
<211> LENGTH: 109
<212> TYPE: PRT
<213> ORGANISM: Homo sapiens

<400> SEQUENCE: 2

Asp Ile Glu Leu Thr Gln Ala Pro Ser Val Ser Val Tyr Pro Gly Gln
 1               5                  10                  15

Thr Ala Arg Ile Thr Cys Ser Gly Asp Ala Leu Pro Lys Gln Tyr Ala
                20                  25                  30

Tyr Trp Tyr Gln Gln Lys Pro Gly Gln Ala Pro Val Val Val Ile Tyr
            35                  40                  45

Lys Asp Ser Glu Arg Pro Ser Gly Ile Ser Glu Arg Phe Ser Gly Ser
 50                  55                  60

Ser Ser Gly Thr Thr Val Thr Leu Thr Ile Ser Gly Val Gln Ala Gly
 65                  70                  75                  80

Asp Glu Ala Asp Tyr Tyr Cys Gln Ser Val Asp Thr Ser Val Ser Tyr
                 85                  90                  95

Tyr Val Val Phe Gly Gly Gly Thr Lys Leu Thr Val Leu
                100                 105

<210> SEQ ID NO 3
<211> LENGTH: 123
<212> TYPE: PRT
<213> ORGANISM: Homo sapiens

<400> SEQUENCE: 3

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Pro Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Asn Gly Asp Ser Tyr Tyr Ala Asp Ser Val
 50                  55                  60

Lys Gly Arg Phe Thr Thr Ser Arg Asp Lys Ser Lys Asn Thr Val Tyr
 65                  70                  75                  80

Leu Gln Met Asn Arg Leu Arg Ala Glu Asp Thr Ala Val Tyr Tyr Cys
                 85                  90                  95

Ala Lys Asp Met Arg Arg Tyr His Tyr Asp Ser Ser Gly Leu His Phe
                100                 105                 110

Trp Gly Gln Gly Thr Leu Val Thr Val Ser Ser
            115                 120

<210> SEQ ID NO 4
<211> LENGTH: 110
<212> TYPE: PRT
<213> ORGANISM: Homo sapiens

<400> SEQUENCE: 4

Asp Ile Met Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Thr Asn
            20                  25                  30

Tyr Val Ser Trp Phe Gln Gln Val Pro Gly Thr Ala Pro Lys Phe Leu
        35                  40                  45

Ile Tyr Asp Asn Tyr Lys Arg Pro Ser Glu Thr Pro Asp Arg Phe Ser
    50                  55                  60

Gly Ser Lys Ser Gly Thr Ser Ala Thr Leu Asp Ile Thr Gly Leu Gln
65                  70                  75                  80

Thr Gly Asp Glu Ala Asn Tyr Tyr Cys Ala Thr Trp Asp Ser Ser Leu
                85                  90                  95

Ser Ala Trp Val Phe Gly Gly Gly Thr Lys Val Thr Val Leu
            100                 105                 110

<210> SEQ ID NO 5
<211> LENGTH: 119
<212> TYPE: PRT
<213> ORGANISM: Homo sapiens

<400> SEQUENCE: 5

Gln Val Gln Leu Val Glu Ser Gly Pro Gly Leu Val Lys Pro Ser Glu
1               5                   10                  15

Thr Leu Ser Leu Thr Cys Arg Val Ser Gly Asp Ser Asn Arg Pro Ser
            20                  25                  30

Tyr Trp Ser Trp Ile Arg Gln Ala Pro Gly Lys Ala Met Glu Trp Ile
        35                  40                  45

Gly Tyr Val Tyr Asp Ser Gly Val Thr Ile Tyr Asn Pro Ser Leu Lys
    50                  55                  60

Gly Arg Val Thr Ile Ser Leu Asp Thr Ser Lys Thr Arg Phe Ser Leu
65                  70                  75                  80

Lys Leu Thr Ser Val Ile Ala Ala Asp Thr Ala Val Tyr Tyr Cys Ala
                85                  90                  95

Arg Glu Arg Phe Asp Arg Thr Ser Tyr Lys Ser Trp Trp Gly Gln Gly
            100                 105                 110

Thr Gln Val Thr Val Ser Ser
        115

<210> SEQ ID NO 6
<211> LENGTH: 108
<212> TYPE: PRT
<213> ORGANISM: Homo sapiens

<400> SEQUENCE: 6

Asp Ile Val Leu Thr Gln Ala Pro Gly Thr Leu Ser Leu Ser Pro Gly
1               5                   10                  15

Asp Arg Ala Thr Leu Ser Cys Arg Ala Ser Gln Arg Leu Gly Gly Thr
            20                  25                  30

Ser Leu Ala Trp Tyr Gln His Arg Ser Gly Gln Ala Pro Arg Leu Ile
        35                  40                  45

Leu Tyr Gly Thr Ser Asn Arg Ala Thr Asp Thr Pro Asp Arg Phe Ser

```
                    50                  55                  60
Gly Ser Gly Ser Gly Thr Asp Phe Val Leu Thr Ile Ser Ser Leu Glu
 65                  70                  75                  80

Pro Glu Asp Phe Ala Val Tyr Tyr Cys Gln Gln Tyr Gly Ser Pro Pro
                 85                  90                  95

Tyr Thr Phe Gly Gln Gly Thr Lys Leu Asp Ile Lys
            100                 105
```

<210> SEQ ID NO 7
<211> LENGTH: 122
<212> TYPE: PRT
<213> ORGANISM: Homo sapiens

<400> SEQUENCE: 7

```
Gln Val Gln Leu Val Gln Ser Gly Gly Thr Leu Val Gln Pro Gly Gly
 1               5                  10                  15

Ser Leu Arg Leu Ser Cys Ala Ala Ser Gly Phe Thr Phe Ser Tyr Tyr
                20                  25                  30

Ser Met Ser Trp Val Arg Gln Ala Pro Gly Lys Gly Leu Glu Trp Val
            35                  40                  45

Ala Asn Ile Lys His Asp Gly Thr Glu Arg Asn Tyr Val Asp Ser Val
 50                  55                  60

Lys Gly Arg Phe Thr Ile Ser Arg Asp Asn Ser Glu Lys Ser Leu Tyr
 65                  70                  75                  80

Leu Gln Met Asn Ser Leu Arg Ala Glu Asp Thr Ala Val Tyr Tyr Cys
                85                  90                  95

Ala Lys Tyr Tyr Tyr Gly Ala Gly Thr Asn Tyr Pro Leu Lys Tyr Trp
            100                 105                 110

Gly Gln Gly Thr Arg Val Thr Val Ser Ser
            115                 120
```

<210> SEQ ID NO 8
<211> LENGTH: 108
<212> TYPE: PRT
<213> ORGANISM: Homo sapiens

<400> SEQUENCE: 8

```
Asp Ile Leu Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Leu
                85                  90                  95

Thr Phe Gly Gly Gly Thr Lys Val Glu Ile Lys Arg
            100                 105
```

<210> SEQ ID NO 9
<211> LENGTH: 116
<212> TYPE: PRT
<213> ORGANISM: Homo sapiens

<400> SEQUENCE: 9

Gln Val Gln Leu Leu Glu Ser Gly Pro Gly Leu Val Arg Pro Ser Asp
1               5                   10                  15

Thr Leu Ser Leu Thr Cys Thr Phe Ser Ala Asp Leu Ser Thr Asn Ala
            20                  25                  30

Tyr Trp Thr Trp Ile Arg Gln Pro Pro Gly Lys Gly Leu Glu Trp Ile
        35                  40                  45

Gly Tyr Met Ser His Ser Gly Gly Arg Asp Tyr Asn Pro Ser Phe Asn
    50                  55                  60

Arg Arg Val Thr Ile Ser Val Asp Thr Ser Lys Asn Gln Val Phe Leu
65                  70                  75                  80

Arg Leu Thr Ser Val Thr Ser Ala Asp Thr Ala Val Tyr Phe Cys Val
                85                  90                  95

Arg Glu Val Gly Ser Tyr Tyr Asp Tyr Trp Gly Gln Gly Ile Leu Val
            100                 105                 110

Thr Val Ser Ser
        115

<210> SEQ ID NO 10
<211> LENGTH: 108
<212> TYPE: PRT
<213> ORGANISM: Homo sapiens

<400> SEQUENCE: 10

Asp Ile Glu Met Thr Gln Ser Pro Ser Ser Leu Ser Ala Ser Val Gly
1               5                   10                  15

Asp Arg Ile Thr Ile Thr Cys Arg Ala Ser Gln Gly Ile Ser Thr Trp
            20                  25                  30

Leu Ala Trp Tyr Gln Gln Lys Pro Gly Lys Ala Pro Lys Ser Leu Ile
        35                  40                  45

Phe Ser Thr Ser Ser Leu His Ser Gly Val Pro Ser Lys Phe Ser Gly
    50                  55                  60

Ser Gly Ser Gly Thr Asp Phe Thr Leu Thr Ile Thr Asn Leu Gln Pro
65                  70                  75                  80

Glu Asp Phe Ala Thr Tyr Tyr Cys Gln Gln Lys Trp Glu Thr Pro Tyr
                85                  90                  95

Ser Phe Gly Gln Gly Thr Lys Leu Asp Met Ile Arg
            100                 105

<210> SEQ ID NO 11
<211> LENGTH: 116
<212> TYPE: PRT
<213> ORGANISM: Homo sapiens

<400> SEQUENCE: 11

Gln Val Gln Leu Val Glu Ser Gly Thr Glu Val Lys Asn Pro Gly Ala
1               5                   10                  15

Ser Val Lys Val Ser Cys Thr Ala Ser Gly Tyr Lys Phe Asp Glu Tyr
            20                  25                  30

Gly Val Ser Trp Val Arg Gln Ser Pro Gly Gln Gly Leu Glu Trp Met
        35                  40                  45

Gly Trp Ile Ser Val Tyr Asn Gly Lys Thr Asn Tyr Ser Gln Asn Phe
    50                  55                  60

Gln Gly Arg Leu Thr Leu Thr Thr Glu Thr Ser Thr Asp Thr Ala Tyr
65                  70                  75                  80

Met Glu Leu Thr Ser Leu Arg Pro Asp Asp Thr Ala Val Tyr Tyr Cys
                85                  90                  95

-continued

Ala Thr Asp Lys Asn Trp Phe Asp Pro Trp Gly Pro Gly Thr Leu Val
            100                 105                 110

Thr Val Ser Ser
        115

<210> SEQ ID NO 12
<211> LENGTH: 107
<212> TYPE: PRT
<213> ORGANISM: Homo sapiens

<400> SEQUENCE: 12

Asp Ile Val Met Thr Gln Ser Pro Ser Ala Ser Gly Ser Pro Gly Gln
1               5                   10                  15

Ser Ile Thr Ile Ser Cys Thr Gly Thr Asn Thr Asp Tyr Asn Tyr Val
            20                  25                  30

Ser Trp Tyr Gln His His Pro Gly Lys Ala Pro Lys Val Ile Ile Tyr
        35                  40                  45

Asp Val Lys Lys Arg Pro Ser Gly Val Pro Ser Arg Phe Ser Gly Ser
    50                  55                  60

Arg Ser Gly Asn Thr Ala Thr Leu Thr Val Ser Gly Leu Gln Thr Glu
65                  70                  75                  80

Asp Glu Ala Asp Tyr Tyr Cys Val Ser Tyr Ala Asp Asn Asn His Tyr
                85                  90                  95

Val Phe Gly Ser Gly Thr Lys Val Thr Val Leu
            100                 105

<210> SEQ ID NO 13
<211> LENGTH: 128
<212> TYPE: PRT
<213> ORGANISM: Homo sapiens

<400> SEQUENCE: 13

Gln Val Gln Leu Val Glu Ser Gly Gly Gly Val Val Gln Pro Gly Gly
1               5                   10                  15

Ser Leu Arg Val Ser Cys Ala Ala Ser Ala Phe Ser Phe Arg Asp Tyr
            20                  25                  30

Gly Ile His Trp Val Arg Gln Ala Pro Gly Lys Gly Leu Gln Trp Val
        35                  40                  45

Ala Val Ile Ser His Asp Gly Lys Lys Phe Tyr Ala Asp Ser Val
    50                  55                  60

Arg Gly Arg Phe Thr Ile Ser Arg Asp Asn Ser Glu Asn Thr Leu Tyr
65                  70                  75                  80

Leu Gln Met Asn Ser Leu Arg Ser Asp Asp Thr Ala Val Tyr Tyr Cys
                85                  90                  95

Ala Arg Leu Val Ala Ser Cys Ser Gly Ser Thr Cys Thr Thr Gln Pro
            100                 105                 110

Ala Ala Phe Asp Ile Trp Gly Pro Gly Thr Leu Val Thr Val Ser Ser
        115                 120                 125

<210> SEQ ID NO 14
<211> LENGTH: 108
<212> TYPE: PRT
<213> ORGANISM: Homo sapiens

<400> SEQUENCE: 14

Asp Ile Met Leu Thr Gln Pro Pro Ser Val Ser Val Ser Pro Gly Gln
1               5                   10                  15

```
Thr Ala Arg Ile Thr Cys Ser Gly Asp Ala Leu Pro Lys Lys Tyr Thr
            20                  25                  30

Tyr Trp Tyr Gln Gln Lys Ser Gly Gln Ala Pro Val Leu Leu Ile Tyr
        35                  40                  45

Glu Asp Arg Lys Arg Pro Ser Glu Ile Pro Glu Arg Phe Ser Ala Phe
50                  55                  60

Thr Ser Trp Thr Thr Ala Thr Leu Thr Ile Thr Gly Ala Gln Val Arg
65                  70                  75                  80

Asp Glu Ala Asp Tyr Tyr Cys Tyr Ser Thr Asp Ile Ser Gly Asp Ile
                85                  90                  95

Gly Val Phe Gly Gly Gly Thr Lys Leu Thr Val Leu
            100                 105
```

<210> SEQ ID NO 15
<211> LENGTH: 120
<212> TYPE: PRT
<213> ORGANISM: Homo sapiens

<400> SEQUENCE: 15

```
Gln Val Gln Leu Leu Glu Ser Gly Ala Asp Met Val Gln Pro Gly Arg
1               5                   10                  15

Ser Leu Arg Leu Ser Cys Ala Ala Ser Gly Phe Asn Phe Arg Thr Tyr
            20                  25                  30

Ala Met His Trp Val Arg Gln Ala Pro Gly Lys Gly Leu Glu Trp Val
        35                  40                  45

Ala Val Met Ser His Asp Gly Tyr Thr Lys Tyr Tyr Ser Asp Ser Val
50                  55                  60

Arg Gly Gln Phe Thr Ile Ser Arg Asp Asn Ser Lys Asn Thr Leu Tyr
65                  70                  75                  80

Leu Gln Met Asn Asn Leu Arg Pro Asp Asp Thr Ala Ile Tyr Tyr Cys
                85                  90                  95

Ala Arg Gly Leu Thr Gly Leu Ser Val Gly Phe Asp Tyr Trp Gly Gln
            100                 105                 110

Gly Thr Leu Val Thr Val Ser Ser
        115                 120
```

<210> SEQ ID NO 16
<211> LENGTH: 111
<212> TYPE: PRT
<213> ORGANISM: Homo sapiens

<400> SEQUENCE: 16

```
Asp Ile Val Leu Thr Gln Ser Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Thr Arg Pro Ser Gly Val Ser Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ser Ser Gly
                85                  90                  95

Ser Thr Pro Ala Leu Phe Gly Gly Gly Thr Gln Leu Thr Val Leu
            100                 105                 110
```

```
<210> SEQ ID NO 17
<211> LENGTH: 122
<212> TYPE: PRT
<213> ORGANISM: Homo sapiens

<400> SEQUENCE: 17

Gln Val Gln Leu Val Gln Ser Gly Gly Gly Leu Val Lys Pro Gly Gly
1               5                   10                  15

Ser Leu Arg Leu Ser Cys Gly Ala Ser Gly Phe Asn Leu Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Arg Ser Ser Tyr Ile Tyr Tyr Ala Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Arg Val Ser Pro Ser Thr Tyr Tyr Tyr Gly Met Asp Val Trp
            100                 105                 110

Gly Gln Gly Thr Thr Val Thr Val Ser Ser
            115                 120

<210> SEQ ID NO 18
<211> LENGTH: 108
<212> TYPE: PRT
<213> ORGANISM: Homo sapiens

<400> SEQUENCE: 18

Asp Ile Val Leu Thr Gln Pro Ser Ser Val Ser Val Ser Pro Gly Gln
1               5                   10                  15

Thr Ala Arg Ile Thr Cys Ser Gly Asp Glu Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Asn Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Leu Thr Val Leu
            100                 105

<210> SEQ ID NO 19
<211> LENGTH: 136
<212> TYPE: PRT
<213> ORGANISM: Homo sapiens

<400> SEQUENCE: 19

Gln Val Gln Leu Val Glu Ser Gly Ala Glu Val Lys Lys Pro Gly Ala
1               5                   10                  15

Leu Val Lys Val Ser Cys Lys Ala Ser Gly Tyr Thr Phe Ser Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Ser Gly Gly Thr Lys Tyr Ala Gln Lys Phe
```

```
                50                  55                  60
Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Phe Cys
                 85                  90                  95

Ala Arg Gly Gly Pro Ser Asn Leu Glu Arg Phe Leu Glu Arg Leu Gln
                100                 105                 110

Pro Arg Tyr Ser Tyr Asp Asp Lys Tyr Ala Met Asp Val Trp Gly Gln
            115                 120                 125

Gly Thr Thr Val Thr Val Ser Ser
            130                 135

<210> SEQ ID NO 20
<211> LENGTH: 109
<212> TYPE: PRT
<213> ORGANISM: Homo sapiens

<400> SEQUENCE: 20

Asp Ile Val Met Thr Gln Ser Pro Gly Thr Leu Ser Leu Ser Pro Gly
  1               5                  10                  15

Ala Arg Ala Thr Leu Ser Cys Arg Ala Ser Gln Ser Val Ser Ser Ile
                 20                  25                  30

Tyr Leu Ala Trp Tyr Gln Gln Lys Pro Gly Gln Ala Pro Arg Leu Leu
             35                  40                  45

Ile Phe Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Tyr Thr Phe Gly Gln Gly Thr Lys Leu Glu Ile Lys Arg
            100                 105

<210> SEQ ID NO 21
<211> LENGTH: 124
<212> TYPE: PRT
<213> ORGANISM: Homo sapiens

<400> SEQUENCE: 21

Gln Val Gln Leu Val Gln Ser Gly Thr Glu Val Lys Lys Pro Gly Glu
  1               5                  10                  15

Ser Leu Lys Ile Ser Cys Glu Gly Ser Arg Tyr Asn Phe Ala Arg Tyr
                 20                  25                  30

Trp Ile Gly Trp Val Arg Gln Met Pro Gly Lys Gly Leu Asp Trp Met
             35                  40                  45

Gly Ile Ile Tyr Pro Gly Asp Ser Asp Thr Arg Tyr Ser Pro Ser Phe
 50                  55                  60

Gln Gly Gln Val Ser Ile Ser Ala Asp Lys Ser Ile Ser Thr Ala Tyr
 65                  70                  75                  80

Leu Gln Trp Asn Ser Leu Lys Ala Ser Asp Thr Ala Met Tyr Tyr Cys
                 85                  90                  95

Ala Arg Leu Gly Ser Glu Leu Gly Val Val Ser Asp Tyr Phe Asp
                100                 105                 110

Ser Trp Gly Gln Gly Thr Leu Val Thr Val Ser Ser
            115                 120
```

```
<210> SEQ ID NO 22
<211> LENGTH: 114
<212> TYPE: PRT
<213> ORGANISM: Homo sapiens

<400> SEQUENCE: 22

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Asp Arg
            20                  25                  30

Ser Asn Asn Lys Asn Cys Val Ala Trp Tyr Gln Gln Lys Pro Gly Gln
        35                  40                  45

Pro Pro Lys Leu Leu Ile Tyr Arg Ala Ala Thr Arg Glu Ser Gly Val
    50                  55                  60

Pro Asp Arg Phe Ser Gly Ser Gly Ser Gly Thr Asp Phe Ser Leu Thr
65                  70                  75                  80

Ile Ser Ser Leu Gln Ala Glu Asp Val Ala Val Tyr Phe Cys Gln Gln
                85                  90                  95

Tyr Tyr Ser Ile Pro Asn Thr Phe Gly Gln Gly Thr Lys Leu Glu Ile
            100                 105                 110

Lys Arg

<210> SEQ ID NO 23
<211> LENGTH: 120
<212> TYPE: PRT
<213> ORGANISM: Homo sapiens

<400> SEQUENCE: 23

Gln Val Gln Leu Val Glu Ser Gly Gly Gly Leu Val Lys Ala Gly Gly
1               5                   10                  15

Ser Leu Arg Leu Ser Cys Val Ala Ser Gly Phe Thr Phe Ser Asp Tyr
            20                  25                  30

Tyr Met Ser Trp Ile Arg Gln Ala Pro Gly Lys Gly Leu Glu Trp Ile
        35                  40                  45

Ser Phe Ile Ser Ser Ser Gly Asp Thr Ile Phe Tyr Ala Asp Ser Val
    50                  55                  60

Lys Gly Arg Phe Thr Val Ser Arg Asp Ser Ala Lys Asn Ser Leu Tyr
65                  70                  75                  80

Leu Gln Met Asn Ser Leu Lys Val Glu Asp Thr Ala Val Tyr Tyr Cys
                85                  90                  95

Ala Arg Lys Gly Val Ser Asp Glu Leu Leu Arg Phe Trp Gly Gln
            100                 105                 110

Gly Thr Leu Val Thr Val Ser Ser
            115                 120

<210> SEQ ID NO 24
<211> LENGTH: 108
<212> TYPE: PRT
<213> ORGANISM: Homo sapiens

<400> SEQUENCE: 24

Asp Ile Val Leu Thr Gln Asp Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45
```

```
Glu Asp Thr Lys Arg Pro Ser Gly Ile Pro Glu Arg Phe Ser Gly Ser
 50                  55                  60
Ser Ser Gly Thr Val Ala Thr Leu Thr Ile Ser Gly Ala Gln Val Glu
 65                  70                  75                  80
Asp Glu Ala Asp Tyr Tyr Cys Tyr Ser Thr Asp Ser Ser Gly Asn Gln
                 85                  90                  95
Arg Val Phe Gly Gly Gly Thr Lys Leu Thr Val Leu
            100                 105

<210> SEQ ID NO 25
<211> LENGTH: 384
<212> TYPE: DNA
<213> ORGANISM: Homo sapiens

<400> SEQUENCE: 25
caggtgcagc tggtgcagtc tgggggaggc ttggtacagc ctggggggtc cctgagactc    60
tcctgtgcag cctctggatt taccttcagt gattatagta tgaactgggt ccgccaggct   120
ccagggaagg gactggaatg gctttcatac attagtcaca ctattactac catatactac   180
gccgactctg tgaagggccg attcaccatc tccagagaca atgccgacag ctcactgtat   240
ctccaaatga acagcctggg agacgaggac acggctgtgt attactgtgc gagagctcca   300
ttagtaaact gtagtactag tggctgccag tccggaagct ggttcgacac ctggggccag   360
ggaaccctgg tcaccgtctc ctca                                         384

<210> SEQ ID NO 26
<211> LENGTH: 327
<212> TYPE: DNA
<213> ORGANISM: Homo sapiens

<400> SEQUENCE: 26
gatatcgagc tgactcaggc accctcggtg tcagtgtatc caggacagac ggccaggatc    60
acctgctctg gagatgcact gccaaagcaa tatgcttatt ggtaccagca gaagccaggc   120
caggcccctg tggtggtgat atataaagac agtgagaggc cctcagggat ctctgagcga   180
ttctctggct ccagctcggg gacaacagtc acgttgacca tcagtggagt ccaggcaggg   240
gacgaggctg actattattg tcaatcagtt gacaccagtg tttcttatta tgtggtcttc   300
ggcggaggga ccaagttgac cgtccta                                      327

<210> SEQ ID NO 27
<211> LENGTH: 369
<212> TYPE: DNA
<213> ORGANISM: Homo sapiens

<400> SEQUENCE: 27
caggtgcagc tggtggagtc cggggggaggc ttggtacagc ctggggggtc cctgagactt    60
tcctgtgccg cctctggatt ccccttcagt agttatgcca tgagttgggt ccgtcaggct   120
ccagggaagg ggctggagtg ggtctcagcc atcagtggca cggcgctga ctcatattac   180 gcagactccg tgaagggccg cttcaccact tccagagaca gtccaagaa tacagtttat   240 ttgcaaatga acagactcag ggccgaggac acggccgtat attactgtgc gaaagatatg   300
cgacggtatc attatgacag tagtggtctg cacttctggg gccagggaac cctggtcacc   360
gtctcctca                                                          369

<210> SEQ ID NO 28
<211> LENGTH: 330
```

<212> TYPE: DNA
<213> ORGANISM: Homo sapiens

<400> SEQUENCE: 28
gatatcatgc tgactcagcc ccctcagtg tctgcggccc ccggacagaa ggtcaccatc    60
tcctgctctg gaagcagctc caacattggg acgaattatg tgtcctggtt ccagcaggtc   120
ccaggaacag cccccaaatt cctcatttat gacaattata acgaccctc agaaactcct   180 gaccgattct ctggctccaa gtctggcacg tcggccaccc tggacatcac cggactccag   240
actggggacg aggccaatta ttactgcgca acatgggaca gtagcctgag tgcttgggtg   300
ttcggcggag ggaccaaggt gaccgtcctg                                    330

<210> SEQ ID NO 29
<211> LENGTH: 357
<212> TYPE: DNA
<213> ORGANISM: Homo sapiens

<400> SEQUENCE: 29
caggtgcagc tggtggagtc cggcccagga ctggtgaagc cttcggagac cctgtccctc    60
acctgcaggg tctctggtga ctccaatcgg ccttcctact ggagctggat caggcaggcc   120
ccagggaagg caatggagtg gataggttat gtctatgaca gtggggtcac catctacaat   180
ccctccctca gggtcgagt cacaatatca ctagacacgt cgaagacgcg gttccctg    240 aaactgacct ctgtgatcgc tgcggacacg gccgtatatt attgtgcgcg agaacgtttt   300
gatcggacat cgtataagag ttggtggggc cagggaacgc aggtcaccgt ctcctca     357

<210> SEQ ID NO 30
<211> LENGTH: 324
<212> TYPE: DNA
<213> ORGANISM: Homo sapiens

<400> SEQUENCE: 30
gatatcgtgc tgactcaggc cccaggcact ctgtctttgt ctccagggga cagagccacc    60
ctctcctgta gggccagtca gcgtcttggc ggcacgtcct tagcctggta ccagcacaga   120
tctggccagg ctcccaggct catcctctac ggaacttcaa acaggccac tgacacccct    180 gacaggttta gtggcagtgg gtctgggaca gacttcgttc tcaccatcag ttccctggag   240
cctgaagatt ttgcagtgta ttactgtcag caatatggca gcccaccgta cacttttggc   300
caggggacca ctctggacat caaa                                           324

<210> SEQ ID NO 31
<211> LENGTH: 366
<212> TYPE: DNA
<213> ORGANISM: Homo sapiens

<400> SEQUENCE: 31
caggtgcagc tggtgcagtc tgggggaacc ttggtccagc cggggggtc cctgagactc      60 tcctgtgcag cctctggatt cacctttagt tactactcga tgagctgggt ccgccaggct   120
ccagggaagg gctggagtg gtggccaac ataaagcacg atggaactga gagaaattat     180
gtggactctg tgaagggccg attcaccatc tccagagaca cagcgagaa gtctctttac    240 ctgcaaatga acagcctgag agccgaggac acggctgtgt attactgtgc gaagtattat   300
tatggtgccg ggactaatta tccccttaag tactggggcc agggaacccg ggtcaccgtc   360
tcctca                                                               366

<210> SEQ ID NO 32
<211> LENGTH: 324
<212> TYPE: DNA
<213> ORGANISM: Homo sapiens

<400> SEQUENCE: 32

| | | | | | |
|---|---|---|---|---|---|
| gatatcctga | tgacccagtc | tccatcctcc | ctgtctgcat | ctgtaggaga | cagagtcacc | 60 |
| atcacttgcc | gggcaagtca | gggcattaga | aatgatttag | gctggtatca | gcagaaacca | 120 |
| gggaaagccc | ctaagctcct | gatctatgct | gcatccagtt | tacaaagtgg | ggtcccatca | 180 |
| aggttcagcg | gcagtggatc | tggcacagat | ttcactctca | ccatcagcag | cctgcagcct | 240 |
| gaagattttg | caacttatta | ctgtctacaa | gattacaatt | acccgctcac | tttcggcgga | 300 |
| gggaccaagg | tggagatcaa | acga | | | | 324 |

<210> SEQ ID NO 33
<211> LENGTH: 348
<212> TYPE: DNA
<213> ORGANISM: Homo sapiens

<400> SEQUENCE: 33

| | | | | | |
|---|---|---|---|---|---|
| caggtgcagc | tgctcgagtc | aggcccaggc | ctggttaggc | cctcggacac | cctgtccctc | 60 |
| acctgcactt | tttccgctga | cctcagcacc | aacgcctatt | ggacctggat | ccggcagccc | 120 |
| ccaggaaagg | gactggagtg | gattggctat | atgtctcata | gtgggggaag | ggattacaat | 180 |
| ccctccttca | accggcgagt | caccatttca | gtggacacgt | cgaagaacca | ggttttcttg | 240 |
| aggctgacgt | cagtgacctc | tgcggacacg | gccgtctatt | tctgtgtgag | agaagtcggc | 300 |
| agttactacg | actactgggg | ccagggaatc | ctggtcaccg | tctcctca | | 348 |

<210> SEQ ID NO 34
<211> LENGTH: 324
<212> TYPE: DNA
<213> ORGANISM: Homo sapiens

<400> SEQUENCE: 34

| | | | | | |
|---|---|---|---|---|---|
| gatatcgaga | tgacccagtc | tccatcctct | ttgtctgcat | ctgtcggaga | cagaatcacc | 60 |
| atcacttgtc | gggcgagtca | gggtattagc | acctggttag | cctggtatca | gcagaaaccg | 120 |
| gggaaagccc | ctaagtccct | gatcttttct | acgtccagcc | tgcatagtgg | ggtcccctca | 180 |
| aagttcagcg | gcagtgggtc | tgggacagac | ttcactctca | ccatcaccaa | cctgcagcct | 240 |
| gaagattttg | caacttatta | ctgccaacag | aaatgggaga | ccccttatag | ttttggccag | 300 |
| gggaccaagc | tggacatgat | acga | | | | 324 |

<210> SEQ ID NO 35
<211> LENGTH: 348
<212> TYPE: DNA
<213> ORGANISM: Homo sapiens

<400> SEQUENCE: 35

| | | | | | |
|---|---|---|---|---|---|
| caggtgcagc | tggtggagtc | tggaactgag | gtgaagaacc | ctggagcctc | agtgaaggtc | 60 |
| tcctgcacgg | cctctggtta | caaatttgac | gaatatggtg | tcagttgggt | gcgacagtcc | 120 |
| cctggacaag | gacttgagtg | gatgggatgg | atcagtgttt | ataatggcaa | gacaaactat | 180 |
| agccagaact | tcagggcag | actcaccctg | accacagaga | catccaccga | cacagcctac | 240 |
| atggagctta | cgagcctcag | acctgacgac | acggccgtct | attactgtgc | gacagacaaa | 300 |
| aactggttcg | accccctgggg | cccgggaacc | ctggtcaccg | tctcctca | | 348 |

<210> SEQ ID NO 36
<211> LENGTH: 321
<212> TYPE: DNA
<213> ORGANISM: Homo sapiens

<400> SEQUENCE: 36

| | | | | | |
|---|---|---|---|---|---|
| gatatcgtga | tgacccagtc | tccctccgcg | tccgggtctc | ctggacagtc | aatcaccatc | 60 |
| tcctgcactg | gaaccaacac | tgattataat | tatgtttcct | ggtaccagca | ccaccccggc | 120 |
| aaagccccca | aagtcattat | ttatgacgtc | aaaaagcggc | cctcggggt | ccctagtcgc | 180 |
| ttctctggct | ccaggtctgg | caacacggcc | accctgaccg | tctctgggct | ccagactgag | 240 |
| gatgaggctg | attattattg | tgtctcatat | gcagacaaca | atcattatgt | cttcggaagt | 300 |
| gggaccaagg | tcaccgtcct | g | | | | 321 |

<210> SEQ ID NO 37
<211> LENGTH: 384
<212> TYPE: DNA
<213> ORGANISM: Homo sapiens

<400> SEQUENCE: 37

| | | | | | |
|---|---|---|---|---|---|
| caggtgcagc | tggtggagtc | cggggggaggc | gtggtccagc | ctggagggtc | cctgagagtc | 60 |
| tcctgtgcag | cctctgcgtt | cagtttcagg | gattatggca | tacactgggt | ccgccaggct | 120 |
| ccaggcaagg | ggctgcaatg | ggtggcggtt | atttcacatg | atggaggtaa | gaaattctat | 180 |
| gcagactccg | tgaggggccg | attcaccatc | tccagagaca | attccgagaa | cacactgtat | 240 |
| ctccaaatga | acagcctgag | atctgacgac | acggctgtct | attactgtgc | gaggctcgtt | 300 |
| gccagttgca | gtggttccac | ctgcacaacg | caacctgctg | cctttgacat | ttggggccca | 360 |
| gggacattgg | tcaccgtctc | ttca | | | | 384 |

<210> SEQ ID NO 38
<211> LENGTH: 324
<212> TYPE: DNA
<213> ORGANISM: Homo sapiens

<400> SEQUENCE: 38

| | | | | | |
|---|---|---|---|---|---|
| gatatcatgc | tgactcagcc | gccctcggtg | tcagtgtccc | caggacaaac | ggccaggatc | 60 |
| acctgctctg | gagatgcatt | gccaaaaaaa | tatacttatt | ggtatcagca | gaagtcaggc | 120 |
| caggcccctg | ttctgctcat | ctatgaggac | aggaaacgac | cctccgagat | ccctgagaga | 180 |
| ttctctgcct | tcacctcatg | gacgacggcc | accttgacta | tcactggggc | ccaggtgaga | 240 |
| gatgaagctg | actactactg | ttattcaaca | gacatcagtg | gtgatatagg | agtgttcggc | 300 |
| ggagggacca | agctgaccgt | ccta | | | | 324 |

<210> SEQ ID NO 39
<211> LENGTH: 333
<212> TYPE: DNA
<213> ORGANISM: Homo sapiens

<400> SEQUENCE: 39

| | | | | | |
|---|---|---|---|---|---|
| gatatcgtgc | tgactcagtc | ggcctccgtg | tctgggtctc | ctggacagtc | gatcaccatc | 60 |
| tcctgcactg | gaaccagcag | tgacgttggt | ggatataact | atgtctcctg | gtaccaacaa | 120 |
| cacccaggca | aagcccccaa | actcatgatt | tatgatgtca | ctactcggcc | ttcagggggtt | 180 |
| tctgatcgct | tctctggctc | caagtctggc | aacacggccc | cctgaccat | ctctgggctg | 240 |

```
caggctgagg acgaggctga ttattattgc agctcatatt caagcggctc cacacctgct    300
ctgtttgggg ggggcaccca gctgaccgtc ctc                                 333
```

<210> SEQ ID NO 40
<211> LENGTH: 333
<212> TYPE: DNA
<213> ORGANISM: Homo sapiens

<400> SEQUENCE: 40

```
gatatcgtgc tgactcagtc ggcctccgtg tctgggtctc ctggacagtc gatcaccatc     60
tcctgcactg gaaccagcag tgacgttggt ggatataact atgtctcctg gtaccaacaa    120
cacccaggca aagcccccaa actcatgatt tatgatgtca ctactcggcc ttcagggggtt   180 tctgatcgct tctctggctc caagtctggc aacacggcct ccctgaccat ctctgggctg    240
caggctgagg acgaggctga ttattattgc agctcatatt caagcggctc cacacctgct    300
ctgtttgggg ggggcaccca gctgaccgtc ctc                                 333
```

<210> SEQ ID NO 41
<211> LENGTH: 366
<212> TYPE: DNA
<213> ORGANISM: Homo sapiens

<400> SEQUENCE: 41

```
caggtgcagc tggtgcagtc tgggggaggc ctggtcaagc ctgggggtc cctgagactc      60 tcctgtggag cctctggatt taacctcagt agttatagca tgaactgggt ccgccaggct    120
ccagggaagg ggctggagtg gtctcatcc attagtagta agagtagtta catatactat     180
gcagactcag tgcagggccg attcaccatc tccagagaca acgccaagaa ctcactgtat    240
ctgcaaatga acagcctgag agccgaggac acggctatat attactgtgc gagagtatct    300
ccgtccacct attattatta tggtatggac gtctggggcc aagggaccac ggtcaccgtc    360
tcctca                                                              366
```

<210> SEQ ID NO 42
<211> LENGTH: 324
<212> TYPE: DNA
<213> ORGANISM: Homo sapiens

<400> SEQUENCE: 42

```
gatatcgtac tcactcagcc gtcctcggtg tcagtgtccc caggacagac ggccaggatc     60
acctgctctg gagatgaatt gccaaagcaa tatgcttatt ggtaccagca gaagccaggc    120
caggcccctg tgttggtaat atataaagac aatgagaggc cctcagggat ccctgagcga    180
ttctctggct ccagctcagg gacaacagtc acgttgacca tcagtggagt ccaggcagaa    240
gacgaggctg actattactg tcaatcagca gacagtagtg gtacttatgt ggtgttcggc    300
ggagggacca agctgaccgt ccta                                          324
```

<210> SEQ ID NO 43
<211> LENGTH: 408
<212> TYPE: DNA
<213> ORGANISM: Homo sapiens

<400> SEQUENCE: 43

```
caggtgcagc tggtggagtc tggggctgag gtgaagaagc ctggggcctt agtgaaggtc     60
tcctgcaagg cttctggata caccttcagc ggctactata tgcactgggt gcgacaggcc    120
cctggacaag gcttgagtg gatgggatgg atcaaccctaa agagtggtgg cacaaagtat   180
```

```
gcacagaagt tcagggccg ggtcaccatg accagggaca cgtccatcag cacagcctac      240
atggagttga gcaggctaag atctgacgac acggccgtgt atttctgtgc gagaggcgga      300
ccttcaaatt tggaacgatt tttggagagg ttacaacccc gctacagtta cgacgacaag      360
tatgctatgg acgtctgggg ccaagggacc acggtcaccg tctcctca                 408
```

<210> SEQ ID NO 44
<211> LENGTH: 328
<212> TYPE: DNA
<213> ORGANISM: Homo sapiens

<400> SEQUENCE: 44

```
gatatcgtga tgacccagtc tccaggcacc ctgtctttgt ctccaggggc aagagccacc      60
ctctcctgca gggccagtca gagtgttagc agcatctatt tagcctggta ccagcagaaa     120
cctggccagg ctcccaggct cctcatcttt ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccgta cacttttggc     300
caggggacca agctggagat caaacgaa                                         328
```

<210> SEQ ID NO 45
<211> LENGTH: 372
<212> TYPE: DNA
<213> ORGANISM: Homo sapiens

<400> SEQUENCE: 45

```
caggtgcagc tggtgcagtc tggaacagaa gtgaaaaagc ccggggagtc tctgaagatc      60
tcctgtgagg gttctcgata caactttgcc aggtactgga tcggctgggt gcgccagatg     120
cccggaaaag gcctggactg gatggggatc atctatcctg gtgactccga taccagatac     180
agcccgtcct tccaaggcca ggtcagcatc tcagccgaca gtccatcag taccgcctac     240 ctgcagtgga acagcctgaa ggcctcggac accgccatgt attattgtgc gagacttggg     300
agcgagcttg gagtggtctc tgattattac tttgactcct ggggccaggg aaccctggtc     360
accgtctcct ca                                                          372
```

<210> SEQ ID NO 46
<211> LENGTH: 342
<212> TYPE: DNA
<213> ORGANISM: Homo sapiens

<400> SEQUENCE: 46

```
gatatcgtgt tgactcagtc tccagactcc ctggctgtgt ctctgggcga gagggccacc      60
atcaactgca gtccagcca gagtgtttta gacaggtcca acaataagaa ctgtgtagct     120
tggtaccagc agaaaccggg acagcctcct aaactgctca tttaccgggc tgctacccgg     180
gaatccgggg tccctgatcg attcagtggc agcgggtctg ggacagactt cagtctcacc     240
atcagcagcc tgcaggctga agatgtggca gtttatttct gtcagcaata ttatagtatt     300
ccgaacactt ttggccaggg gaccaagctg gagatcaaac ga                         342
```

<210> SEQ ID NO 47
<211> LENGTH: 360
<212> TYPE: DNA
<213> ORGANISM: Homo sapiens

<400> SEQUENCE: 47

```
caggtgcagc tggtggagtc tgggggaggc ttggtcaagg ctggagggtc cctgagactc      60
tcctgtgtag cctctggatt caccttcagc gactactaca tgtcctggat tcgccaggct     120
ccagggaagg ggctggagtg gatttcattt attagtagta gtggtgatac catattttac     180
gcagactctg tgaagggccg attcaccgtc tccagggaca cgccaagaa ctcactgtat      240 cttcaaatga acagcctgaa agtcgaggac acggccgtgt attactgtgc gaggaagggg    300
gtgtccgacg aggaactact gcgcttctgg ggccagggaa ccctggtcac cgtctcctca    360

<210> SEQ ID NO 48
<211> LENGTH: 324
<212> TYPE: DNA
<213> ORGANISM: Homo sapiens

<400> SEQUENCE: 48
gatatcgtgc tgactcagga cccctcggtg tcagtgtccc caggacaaac ggccaggatc     60
acctgctctg gagatgcatt gccaaaaaaa tatgcttatt ggtaccagca gaagtcaggc   120
caggcccctg tgctggtcat ctatgaggac accaaacgac cctccgggat ccctgagaga    180
ttctctggct ccagctcagg gacagtggcc accttgacta tcagtggggc ccaggtggag    240
gatgaagctg actactattg ttactcaaca gacagcagcg gtaatcagag ggtattcggc    300
ggagggacca agctgaccgt ccta                                            324

<210> SEQ ID NO 49
<211> LENGTH: 16
<212> TYPE: PRT
<213> ORGANISM: H. influenzae

<400> SEQUENCE: 49

Ile Glu Tyr Leu Ser Asp Lys Tyr His Leu Ser Lys Gln Asp Thr Lys
1               5                   10                  15

<210> SEQ ID NO 50
<211> LENGTH: 23
<212> TYPE: PRT
<213> ORGANISM: H. influenzae

<400> SEQUENCE: 50

Arg Asp Lys Ser Ser Arg Pro Gly Arg Asn Pro Lys Thr Gly Asp Val
1               5                   10                  15

Val Ala Ala Ser Ala Arg Arg
            20

<210> SEQ ID NO 51
<211> LENGTH: 11
<212> TYPE: PRT
<213> ORGANISM: H. influenzae

<400> SEQUENCE: 51

Gln Lys Leu Arg Ala Arg Val Glu Lys Thr Lys
1               5                   10
```